(12) United States Patent
Stokes et al.

(10) Patent No.: US 9,474,540 B2
(45) Date of Patent: Oct. 25, 2016

(54) LAPAROSCOPIC DEVICE WITH COMPOUND ANGULATION

(75) Inventors: Michael J. Stokes, Cincinnati, OH (US); Christopher J. Hess, Cincinnati, OH (US); William B. Weisenburgh, II, Maineville, OH (US)

(73) Assignee: Ethicon-Endo-Surgery, Inc., Cincinnati, OH (US)

( * ) Notice: Subject to any disclaimer, the term of this patent is extended or adjusted under 35 U.S.C. 154(b) by 1075 days.

(21) Appl. No.: 12/775,727

(22) Filed: May 7, 2010

(65) Prior Publication Data
US 2011/0087236 A1    Apr. 14, 2011

Related U.S. Application Data

(60) Provisional application No. 61/249,780, filed on Oct. 8, 2009.

(51) Int. Cl.
*A61B 17/29* (2006.01)
*A61B 17/34* (2006.01)

(52) U.S. Cl.
CPC .......... *A61B 17/29* (2013.01); *A61B 2017/292* (2013.01); *A61B 2017/2908* (2013.01); *A61B 2017/2912* (2013.01); *A61B 2017/2919* (2013.01); *A61B 2017/2922* (2013.01); *A61B 2017/3445* (2013.01)

(58) Field of Classification Search
CPC .............. A61B 17/29; A61B 17/0218; A61B 2017/2901; A61B 2017/2902; A61B 2017/2908; A61B 2017/2912; A61B 2017/2916; A61B 2017/2919; A61B 2017/292; A61B 2017/2922; A61B 2017/3445; A61B 1/0055; A61B 1/008; A61B 90/50

USPC ............ 606/139, 205, 208; 227/175.1
See application file for complete search history.

(56) References Cited

U.S. PATENT DOCUMENTS

| 2,129,391 A | 9/1938 | Wappler |
| 2,765,930 A | 10/1956 | Geer et al. |
| 3,402,710 A | 9/1968 | Paleschuck |

(Continued)

FOREIGN PATENT DOCUMENTS

| DE | 4300307 A1 | 7/1994 |
| DE | 4324254 C1 | 1/1995 |

(Continued)

OTHER PUBLICATIONS

U.S. Appl. No. 12/399,473, filed Mar. 6, 2009 entitled Methods and Devices for Providing Access Into a Body Cavity.

(Continued)

*Primary Examiner* — Diane Yabut
(74) *Attorney, Agent, or Firm* — Mintz Levin Cohn Ferris Glovsky and Popeo, P.C.

(57) ABSTRACT

Methods and devices are provided for performing minimally invasive surgical procedures. In one embodiment, a surgical device is provided that includes an elongate shaft having a distal portion configured to be movable between a first configuration in which the distal portion of the shaft is substantially straight or linear and a second configuration in which the distal portion of the shaft is bent at a compound angle. The shaft's distal portion can be configured to be articulated in a wide range of compound angles and can be configured to be selectively locked in a fixed position anywhere within that range.

22 Claims, 8 Drawing Sheets

(56) References Cited

U.S. PATENT DOCUMENTS

| | | |
|---|---|---|
| 3,503,396 A | 3/1970 | Pierie et al. |
| 3,654,965 A | 4/1972 | Gramain |
| 4,041,931 A | 8/1977 | Elliott et al. |
| 4,048,987 A | 9/1977 | Hurson |
| 4,112,932 A | 9/1978 | Chiulli |
| 4,120,302 A | 10/1978 | Ziegler |
| 4,203,430 A | 5/1980 | Takahashi |
| 4,306,545 A | 12/1981 | Ivan et al. |
| 4,373,532 A | 2/1983 | Hill et al. |
| 4,402,683 A | 9/1983 | Kopman |
| 4,417,888 A | 11/1983 | Cosentino et al. |
| 4,559,947 A | 12/1985 | Renger et al. |
| 4,608,977 A | 9/1986 | Brown |
| 4,669,473 A | 6/1987 | Richards et al. |
| 4,821,719 A | 4/1989 | Fogarty |
| 4,831,070 A | 5/1989 | McInally et al. |
| 4,880,015 A | 11/1989 | Nierman |
| 5,020,514 A | 6/1991 | Heckele |
| 5,027,800 A | 7/1991 | Rowland |
| 5,058,603 A * | 10/1991 | Doi et al. ............... 600/587 |
| 5,141,498 A | 8/1992 | Christian |
| 5,183,471 A | 2/1993 | Wilk |
| 5,197,955 A | 3/1993 | Stephens et al. |
| 5,201,742 A | 4/1993 | Hasson |
| 5,207,213 A | 5/1993 | Auhll et al. |
| 5,209,737 A | 5/1993 | Ritchart et al. |
| 5,209,741 A | 5/1993 | Spaeth |
| 5,209,747 A | 5/1993 | Knoepfler |
| 5,269,772 A | 12/1993 | Wilk |
| 5,275,614 A | 1/1994 | Haber et al. |
| 5,284,128 A | 2/1994 | Hart |
| 5,308,336 A | 5/1994 | Hart et al. |
| 5,312,023 A | 5/1994 | Green et al. |
| 5,329,923 A | 7/1994 | Lundquist |
| 5,330,437 A | 7/1994 | Durman |
| 5,330,502 A | 7/1994 | Hassler et al. |
| 5,342,396 A | 8/1994 | Cook |
| 5,345,927 A | 9/1994 | Bonutti |
| 5,350,391 A | 9/1994 | Iacovelli |
| 5,360,428 A | 11/1994 | Hutchinson, Jr. |
| 5,362,294 A | 11/1994 | Seitzinger |
| 5,366,478 A | 11/1994 | Brinkerhoff et al. |
| 5,368,597 A | 11/1994 | Pagedas |
| 5,374,277 A | 12/1994 | Hassler |
| 5,381,943 A * | 1/1995 | Allen et al. ............... 227/177.1 |
| 5,383,888 A | 1/1995 | Zvenyatsky et al. |
| 5,385,553 A | 1/1995 | Hart et al. |
| 5,385,560 A | 1/1995 | Wulf |
| 5,391,154 A | 2/1995 | Young |
| 5,398,617 A | 3/1995 | Deandrea |
| 5,403,342 A | 4/1995 | Tovey et al. |
| 5,417,203 A | 5/1995 | Tovey et al. |
| 5,419,339 A | 5/1995 | Palmer |
| 5,441,483 A | 8/1995 | Avitall |
| 5,443,452 A | 8/1995 | Hart et al. |
| 5,443,484 A | 8/1995 | Kirsch et al. |
| 5,445,648 A | 8/1995 | Cook |
| 5,456,684 A | 10/1995 | Schmidt et al. |
| 5,480,410 A | 1/1996 | Cuschieri et al. |
| 5,489,256 A | 2/1996 | Adair |
| 5,489,290 A | 2/1996 | Furnish |
| 5,501,653 A | 3/1996 | Chin |
| 5,514,157 A | 5/1996 | Nicholas et al. |
| 5,520,609 A | 5/1996 | Moll et al. |
| 5,520,678 A | 5/1996 | Heckele et al. |
| 5,545,123 A | 8/1996 | Ortiz et al. |
| 5,545,179 A | 8/1996 | Williamson, IV |
| 5,547,458 A | 8/1996 | Ortiz et al. |
| 5,549,637 A | 8/1996 | Crainich |
| 5,569,205 A | 10/1996 | Hart et al. |
| 5,569,254 A | 10/1996 | Carlson et al. |
| 5,571,090 A | 11/1996 | Sherts |
| 5,571,129 A | 11/1996 | Porter |
| 5,573,520 A | 11/1996 | Schwartz et al. |
| 5,578,048 A | 11/1996 | Pasqualucci et al. |
| 5,582,577 A | 12/1996 | Lund et al. |
| 5,582,617 A | 12/1996 | Klieman et al. |
| 5,584,850 A | 12/1996 | Hart et al. |
| 5,586,977 A | 12/1996 | Dorsey, III |
| 5,591,182 A | 1/1997 | Johnson |
| 5,595,193 A | 1/1997 | Walus et al. |
| 5,607,450 A | 3/1997 | Zvenyatsky et al. |
| 5,609,601 A | 3/1997 | Kolesa et al. |
| 5,618,291 A | 4/1997 | Thompson et al. |
| 5,618,294 A | 4/1997 | Aust et al. |
| 5,624,381 A | 4/1997 | Kieturakis |
| 5,626,608 A | 5/1997 | Cuny et al. |
| 5,630,831 A | 5/1997 | Lahr |
| 5,632,432 A | 5/1997 | Schulze et al. |
| 5,632,734 A | 5/1997 | Galel et al. |
| 5,634,882 A | 6/1997 | Gagner |
| 5,634,883 A | 6/1997 | Chin et al. |
| 5,634,911 A | 6/1997 | Hermann et al. |
| 5,634,937 A | 6/1997 | Mollenauer et al. |
| 5,636,645 A | 6/1997 | Ou |
| 5,640,977 A | 6/1997 | Leahy et al. |
| 5,643,283 A | 7/1997 | Younker |
| 5,643,301 A | 7/1997 | Mollenauer |
| 5,647,372 A | 7/1997 | Tovey et al. |
| 5,653,705 A | 8/1997 | de la Torre et al. |
| 5,665,093 A | 9/1997 | Atkins et al. |
| 5,667,527 A | 9/1997 | Cook |
| 5,672,168 A | 9/1997 | de la Torre et al. |
| 5,676,146 A | 10/1997 | Scarborough |
| 5,676,657 A | 10/1997 | Yoon |
| 5,681,324 A | 10/1997 | Kammerer et al. |
| 5,695,448 A | 12/1997 | Kimura et al. |
| 5,700,275 A | 12/1997 | Bell et al. |
| 5,704,534 A | 1/1998 | Huitema et al. |
| 5,713,919 A | 2/1998 | Lahr |
| 5,716,327 A | 2/1998 | Warner et al. |
| 5,716,407 A | 2/1998 | Knapp et al. |
| 5,728,121 A | 3/1998 | Bimbo et al. |
| 5,735,289 A | 4/1998 | Pfeffer et al. |
| 5,743,456 A * | 4/1998 | Jones et al. ............... 227/176.1 |
| 5,743,851 A | 4/1998 | Moll et al. |
| 5,766,205 A | 6/1998 | Zvenyatsky et al. |
| 5,772,654 A | 6/1998 | Leyva |
| 5,782,812 A | 7/1998 | Hart et al. |
| 5,782,859 A | 7/1998 | Nicholas et al. |
| 5,792,165 A | 8/1998 | Klieman et al. |
| 5,797,959 A | 8/1998 | Castro et al. |
| 5,803,919 A | 9/1998 | Hart et al. |
| 5,813,409 A | 9/1998 | Leahy et al. |
| 5,814,058 A | 9/1998 | Carlson et al. |
| 5,816,257 A | 10/1998 | Chin |
| 5,827,319 A | 10/1998 | Carlson et al. |
| 5,827,323 A | 10/1998 | Klieman et al. |
| 5,833,692 A | 11/1998 | Cesarini et al. |
| 5,836,960 A | 11/1998 | Kolesa et al. |
| 5,840,078 A | 11/1998 | Yerys |
| 5,853,395 A | 12/1998 | Crook et al. |
| 5,865,807 A | 2/1999 | Blake, III |
| 5,872,859 A | 2/1999 | Gur et al. |
| 5,876,447 A | 3/1999 | Arnett |
| 5,891,013 A | 4/1999 | Thompson |
| 5,893,878 A | 4/1999 | Pierce |
| 5,906,577 A | 5/1999 | Beane et al. |
| 5,921,956 A | 7/1999 | Grinberg et al. |
| 5,941,890 A | 8/1999 | Voegele et al. |
| 5,947,922 A | 9/1999 | MacLeod |
| 5,957,913 A | 9/1999 | de la Torre et al. |
| 5,971,995 A | 10/1999 | Rousseau |
| 5,977,431 A | 11/1999 | Knapp et al. |
| 5,990,382 A | 11/1999 | Fox |
| 6,007,561 A | 12/1999 | Bourque et al. |
| 6,024,708 A | 2/2000 | Bales et al. |
| 6,024,736 A | 2/2000 | de la Torre et al. |
| 6,027,522 A | 2/2000 | Palmer |
| 6,033,428 A | 3/2000 | Sardella |
| RE36,702 E | 5/2000 | Green et al. |
| 6,074,419 A | 6/2000 | Healy et al. |
| 6,077,287 A | 6/2000 | Taylor et al. |
| 6,077,288 A | 6/2000 | Shimomura et al. |

(56) References Cited

U.S. PATENT DOCUMENTS

| | | |
|---|---|---|
| 6,086,603 A | 7/2000 | Termin et al. |
| 6,093,141 A | 7/2000 | Mosseri et al. |
| 6,110,154 A | 8/2000 | Shimomura et al. |
| 6,110,182 A | 8/2000 | Mowlai-Ashtiani |
| 6,120,513 A | 9/2000 | Bailey et al. |
| 6,123,689 A | 9/2000 | To et al. |
| 6,126,671 A | 10/2000 | Richards et al. |
| 6,132,385 A | 10/2000 | Vain |
| 6,149,642 A | 11/2000 | Gerhart et al. |
| 6,156,045 A | 12/2000 | Ulbrich et al. |
| 6,156,184 A | 12/2000 | Antonucci et al. |
| 6,159,200 A | 12/2000 | Verdura et al. |
| 6,162,196 A | 12/2000 | Hart et al. |
| 6,162,208 A | 12/2000 | Hipps |
| 6,165,184 A | 12/2000 | Verdura et al. |
| 6,171,282 B1 | 1/2001 | Ragsdale |
| 6,197,034 B1 | 3/2001 | Gvozdic et al. |
| 6,217,555 B1 | 4/2001 | Hart et al. |
| 6,220,248 B1 | 4/2001 | Voegele et al. |
| 6,228,055 B1 | 5/2001 | Foerster et al. |
| 6,245,011 B1 | 6/2001 | Dudda et al. |
| 6,245,052 B1 | 6/2001 | Orth et al. |
| 6,248,062 B1 | 6/2001 | Adler et al. |
| 6,258,069 B1 | 7/2001 | Carpentier et al. |
| 6,258,102 B1 | 7/2001 | Pagedas |
| 6,261,302 B1 | 7/2001 | Voegele et al. |
| 6,264,599 B1 | 7/2001 | Slater et al. |
| 6,290,705 B1 | 9/2001 | Chan et al. |
| 6,293,966 B1 | 9/2001 | Frantzen |
| 6,315,770 B1 | 11/2001 | de la Torre et al. |
| 6,319,246 B1 | 11/2001 | de la Torre et al. |
| 6,347,940 B1 | 2/2002 | Gordils Wallis et al. |
| 6,348,034 B1 | 2/2002 | Thompson |
| 6,352,503 B1 | 3/2002 | Matsui et al. |
| 6,400,979 B1 | 6/2002 | Stoianovici et al. |
| 6,402,687 B1 | 6/2002 | Ouchi |
| 6,425,903 B1 | 7/2002 | Voegele |
| 6,443,960 B1 | 9/2002 | Brabrand et al. |
| 6,447,443 B1 | 9/2002 | Keogh et al. |
| 6,447,489 B1 | 9/2002 | Peterson |
| 6,454,783 B1 | 9/2002 | Piskun |
| 6,456,184 B1 | 9/2002 | Vu et al. |
| 6,458,077 B1 | 10/2002 | Boebel et al. |
| 6,471,714 B1 | 10/2002 | Kim |
| 6,485,467 B1 | 11/2002 | Crook et al. |
| 6,494,211 B1 * | 12/2002 | Boyd et al. .................. 128/898 |
| 6,551,270 B1 | 4/2003 | Bimbo et al. |
| 6,551,282 B1 | 4/2003 | Exline et al. |
| 6,578,577 B2 | 6/2003 | Bonadio et al. |
| 6,579,304 B1 | 6/2003 | Hart et al. |
| 6,589,167 B1 | 7/2003 | Shimomura et al. |
| 6,605,063 B2 | 8/2003 | Bousquet |
| 6,613,068 B2 | 9/2003 | Ouchi et al. |
| 6,623,426 B2 | 9/2003 | Bonadio et al. |
| 6,634,883 B2 | 10/2003 | Ranalli |
| RE38,335 E | 11/2003 | Aust et al. |
| 6,663,641 B1 | 12/2003 | Kovac et al. |
| 6,665,554 B1 | 12/2003 | Charles et al. |
| 6,666,854 B1 | 12/2003 | Lange et al. |
| 6,669,674 B1 | 12/2003 | Macoviak et al. |
| 6,673,092 B1 | 1/2004 | Bacher |
| 6,689,122 B2 | 2/2004 | Yamamoto |
| 6,706,033 B1 | 3/2004 | Martinez et al. |
| 6,706,050 B1 | 3/2004 | Giannadakis |
| 6,725,083 B1 | 4/2004 | Burbank et al. |
| 6,764,473 B2 | 7/2004 | Morton |
| 6,766,186 B1 | 7/2004 | Hoyns et al. |
| 6,807,965 B1 | 10/2004 | Hickle |
| 6,810,880 B1 | 11/2004 | Jennings, Jr. et al. |
| 6,818,007 B1 | 11/2004 | Dampney et al. |
| 6,821,247 B2 | 11/2004 | Vierra et al. |
| 6,846,287 B2 | 1/2005 | Bonadio et al. |
| 6,872,433 B2 | 3/2005 | Seward et al. |
| 6,908,430 B2 | 6/2005 | Caldwell et al. |
| 6,913,613 B2 | 7/2005 | Schwarz et al. |
| 6,936,061 B2 | 8/2005 | Sasaki |
| 6,939,296 B2 | 9/2005 | Ewers et al. |
| 6,945,932 B1 | 9/2005 | Caldwell et al. |
| 6,966,876 B2 | 11/2005 | Irion et al. |
| 6,972,026 B1 | 12/2005 | Caldwell et al. |
| 6,994,712 B1 | 2/2006 | Fisher et al. |
| 7,008,377 B2 | 3/2006 | Beane et al. |
| 7,014,628 B2 | 3/2006 | Bousquet |
| 7,021,173 B2 | 4/2006 | Stoianovici et al. |
| 7,047,063 B2 | 5/2006 | Burbank et al. |
| 7,052,454 B2 | 5/2006 | Taylor |
| 7,083,576 B2 | 8/2006 | Zarins et al. |
| 7,083,626 B2 | 8/2006 | Hart et al. |
| 7,087,071 B2 | 8/2006 | Nicholas et al. |
| 7,118,528 B1 | 10/2006 | Piskun |
| 7,147,650 B2 | 12/2006 | Lee |
| 7,163,510 B2 | 1/2007 | Kahle et al. |
| 7,201,734 B2 | 4/2007 | Hickle |
| 7,208,005 B2 | 4/2007 | Frecker et al. |
| 7,214,185 B1 | 5/2007 | Rosney et al. |
| 7,247,154 B2 | 7/2007 | Hickle |
| 7,311,661 B2 | 12/2007 | Heinrich |
| 7,331,661 B2 | 2/2008 | Silverbrook et al. |
| 7,331,750 B2 | 2/2008 | Merz et al. |
| 7,338,473 B2 | 3/2008 | Campbell et al. |
| 7,344,547 B2 | 3/2008 | Piskun |
| 7,347,862 B2 | 3/2008 | Layer |
| 7,416,533 B2 | 8/2008 | Gellman et al. |
| 7,615,005 B2 | 11/2009 | Stefanchik et al. |
| 7,691,095 B2 | 4/2010 | Bednarek et al. |
| 7,909,220 B2 | 3/2011 | Viola |
| 7,985,239 B2 | 7/2011 | Suzuki |
| 7,988,699 B2 | 8/2011 | Martz et al. |
| 8,083,667 B2 | 12/2011 | Cooper et al. |
| 8,182,418 B2 | 5/2012 | Durant et al. |
| 8,562,592 B2 | 10/2013 | Conlon et al. |
| 8,758,232 B2 | 6/2014 | Graham et al. |
| 9,226,760 B2 | 1/2016 | Shelton, IV |
| 2001/0034528 A1 | 10/2001 | Foerster et al. |
| 2001/0053510 A1 | 12/2001 | Ranalli |
| 2002/0007112 A1 | 1/2002 | Rupp et al. |
| 2002/0026201 A1 | 2/2002 | Foerster et al. |
| 2002/0103434 A1 | 8/2002 | Swanbom |
| 2002/0156432 A1 | 10/2002 | Racenet et al. |
| 2002/0156497 A1 | 10/2002 | Nagase et al. |
| 2002/0173805 A1 | 11/2002 | Matsuno et al. |
| 2002/0193815 A1 | 12/2002 | Foerster et al. |
| 2003/0028179 A1 | 2/2003 | Piskun |
| 2003/0028207 A1 | 2/2003 | Lang et al. |
| 2003/0073882 A1 | 4/2003 | Smid et al. |
| 2003/0100814 A1 | 5/2003 | Kindlein |
| 2003/0109898 A1 * | 6/2003 | Schwarz et al. .............. 606/205 |
| 2003/0113540 A1 | 6/2003 | Anderson et al. |
| 2003/0114838 A1 | 6/2003 | O'Neill et al. |
| 2003/0120285 A1 | 6/2003 | Kortenbach |
| 2003/0135204 A1 | 7/2003 | Lee et al. |
| 2003/0139756 A1 | 7/2003 | Brustad |
| 2003/0206860 A1 | 11/2003 | Bleyer et al. |
| 2003/0208207 A1 | 11/2003 | Layer |
| 2003/0225420 A1 | 12/2003 | Wardle |
| 2003/0229338 A1 | 12/2003 | Irion et al. |
| 2003/0236549 A1 | 12/2003 | Bonadio et al. |
| 2004/0015185 A1 | 1/2004 | Ewers et al. |
| 2004/0023161 A1 | 2/2004 | Yamaguchi et al. |
| 2004/0024304 A1 | 2/2004 | Foerster et al. |
| 2004/0068291 A1 | 4/2004 | Suzuki |
| 2004/0106942 A1 | 6/2004 | Taylor et al. |
| 2004/0106986 A1 | 6/2004 | Andersson et al. |
| 2004/0138525 A1 | 7/2004 | Saadat et al. |
| 2004/0138528 A1 | 7/2004 | Richter et al. |
| 2004/0147933 A1 | 7/2004 | McGovern |
| 2004/0167545 A1 | 8/2004 | Sadler et al. |
| 2004/0193146 A1 | 9/2004 | Lee et al. |
| 2004/0193212 A1 | 9/2004 | Taniguchi et al. |
| 2004/0215063 A1 | 10/2004 | Bonadio et al. |
| 2004/0225323 A1 | 11/2004 | Nagase et al. |
| 2004/0230160 A1 | 11/2004 | Blanco |
| 2004/0230161 A1 | 11/2004 | Zeiner |
| 2004/0243108 A1 | 12/2004 | Suzuki |

(56) References Cited

U.S. PATENT DOCUMENTS

| | | |
|---|---|---|
| 2004/0254426 A1 | 12/2004 | Wenchell |
| 2004/0260198 A1 | 12/2004 | Rothberg et al. |
| 2004/0260337 A1 | 12/2004 | Freed |
| 2005/0020884 A1 | 1/2005 | Hart et al. |
| 2005/0033312 A1 | 2/2005 | Suzuki |
| 2005/0033342 A1 | 2/2005 | Hart et al. |
| 2005/0033357 A1 | 2/2005 | Braun |
| 2005/0049580 A1* | 3/2005 | Brock et al. ............... 606/1 |
| 2005/0085842 A1 | 4/2005 | Eversull et al. |
| 2005/0090809 A1 | 4/2005 | Cooper et al. |
| 2005/0107809 A1 | 5/2005 | Litscher et al. |
| 2005/0124912 A1 | 6/2005 | Griego et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0222582 A1 | 10/2005 | Wenchell |
| 2005/0228224 A1 | 10/2005 | Okada et al. |
| 2005/0267419 A1 | 12/2005 | Smith |
| 2005/0273084 A1 | 12/2005 | Hinman et al. |
| 2005/0273132 A1 | 12/2005 | Shluzas et al. |
| 2005/0277946 A1 | 12/2005 | Greenhalgh |
| 2006/0016853 A1 | 1/2006 | Racenet |
| 2006/0020241 A1 | 1/2006 | Piskun et al. |
| 2006/0020281 A1 | 1/2006 | Smith |
| 2006/0020287 A1 | 1/2006 | Lee et al. |
| 2006/0042636 A1 | 3/2006 | Nalagatla et al. |
| 2006/0071432 A1 | 4/2006 | Staudner |
| 2006/0094933 A1* | 5/2006 | Goldfarb et al. ............. 600/229 |
| 2006/0149137 A1 | 7/2006 | Pingleton et al. |
| 2006/0206145 A1 | 9/2006 | Griego et al. |
| 2006/0212062 A1 | 9/2006 | Farascioni |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0229641 A1 | 10/2006 | Gupta et al. |
| 2006/0229665 A1 | 10/2006 | Wales et al. |
| 2006/0241651 A1 | 10/2006 | Wilk |
| 2006/0241671 A1 | 10/2006 | Greenhalgh |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0259071 A1 | 11/2006 | Nicholas et al. |
| 2006/0259073 A1 | 11/2006 | Miyamoto et al. |
| 2006/0264706 A1 | 11/2006 | Piskun |
| 2006/0270911 A1 | 11/2006 | Voegele et al. |
| 2007/0027468 A1 | 2/2007 | Wales et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088277 A1 | 4/2007 | McGinley et al. |
| 2007/0106317 A1 | 5/2007 | Shelton et al. |
| 2007/0118021 A1 | 5/2007 | Pokorney |
| 2007/0151566 A1 | 7/2007 | Kahle et al. |
| 2007/0156119 A1 | 7/2007 | Wallace et al. |
| 2007/0162072 A1 | 7/2007 | Nicholas et al. |
| 2007/0179525 A1 | 8/2007 | Frecker et al. |
| 2007/0185453 A1 | 8/2007 | Michael et al. |
| 2007/0208312 A1 | 9/2007 | Norton et al. |
| 2007/0244358 A1 | 10/2007 | Lee |
| 2007/0250113 A1 | 10/2007 | Hegeman et al. |
| 2007/0255219 A1 | 11/2007 | Vaugh et al. |
| 2007/0260114 A1 | 11/2007 | Miyamoto et al. |
| 2008/0027476 A1 | 1/2008 | Piskun |
| 2008/0039892 A1 | 2/2008 | Mitsuishi et al. |
| 2008/0045803 A1 | 2/2008 | Williams et al. |
| 2008/0051631 A1 | 2/2008 | Dejima et al. |
| 2008/0051739 A1 | 2/2008 | McFarlane |
| 2008/0064921 A1 | 3/2008 | Larkin et al. |
| 2008/0065021 A1 | 3/2008 | Jenkins et al. |
| 2008/0065107 A1 | 3/2008 | Larkin et al. |
| 2008/0105730 A1 | 5/2008 | Racenet et al. |
| 2008/0119821 A1 | 5/2008 | Agnihotri et al. |
| 2008/0147113 A1* | 6/2008 | Nobis et al. ............... 606/205 |
| 2008/0154299 A1 | 6/2008 | Livneh |
| 2008/0177134 A1 | 7/2008 | Miyamoto et al. |
| 2008/0183044 A1 | 7/2008 | Colleran et al. |
| 2008/0188891 A1 | 8/2008 | Frank et al. |
| 2008/0255420 A1 | 10/2008 | Lee et al. |
| 2008/0255519 A1 | 10/2008 | Piskun et al. |
| 2008/0255608 A1 | 10/2008 | Hinman et al. |
| 2008/0262492 A1 | 10/2008 | Lee |
| 2008/0269727 A1 | 10/2008 | Lee |
| 2008/0294154 A1 | 11/2008 | Ibrahim et al. |
| 2008/0294191 A1 | 11/2008 | Lee |
| 2009/0005799 A1 | 1/2009 | Franer et al. |
| 2009/0062618 A1 | 3/2009 | Drew et al. |
| 2009/0084826 A1 | 4/2009 | Shah et al. |
| 2009/0088792 A1 | 4/2009 | Hoell, Jr. et al. |
| 2009/0112230 A1 | 4/2009 | Jinno |
| 2009/0171147 A1 | 7/2009 | Lee et al. |
| 2009/0206129 A1 | 8/2009 | Doll et al. |
| 2009/0306658 A1 | 12/2009 | Nobis et al. |
| 2009/0326325 A1* | 12/2009 | Naito et al. ............... 600/141 |
| 2010/0057121 A1 | 3/2010 | Piskun et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094289 A1 | 4/2010 | Taylor et al. |
| 2010/0130817 A1 | 5/2010 | Conlon |
| 2010/0179540 A1 | 7/2010 | Marczyk et al. |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2010/0261975 A1 | 10/2010 | Huey et al. |
| 2010/0312060 A1 | 12/2010 | Widenhouse et al. |
| 2010/0312061 A1 | 12/2010 | Hess et al. |
| 2010/0312064 A1 | 12/2010 | Weisenburgh, II et al. |
| 2010/0312065 A1 | 12/2010 | Shelton, IV et al. |
| 2010/0331857 A1 | 12/2010 | Doyle et al. |
| 2011/0027269 A1 | 2/2011 | Marrotta et al. |
| 2011/0028793 A1 | 2/2011 | Martin et al. |
| 2011/0028794 A1 | 2/2011 | Widenhouse et al. |
| 2011/0087269 A1 | 4/2011 | Stokes et al. |
| 2011/0230875 A1 | 9/2011 | Walberg et al. |
| 2011/0275901 A1 | 11/2011 | Shelton, IV |
| 2011/0276057 A1 | 11/2011 | Conlon et al. |
| 2011/0276083 A1 | 11/2011 | Shelton, IV et al. |
| 2011/0276084 A1 | 11/2011 | Shelton, IV |
| 2012/0024099 A1 | 2/2012 | Main |
| 2012/0078243 A1 | 3/2012 | Worrell et al. |
| 2014/0039518 A1 | 2/2014 | Conlon et al. |
| 2015/0119918 A1 | 4/2015 | Blase et al. |

FOREIGN PATENT DOCUMENTS

| | | |
|---|---|---|
| DE | 9419138 U1 | 3/1995 |
| DE | 19520717 A1 | 12/1996 |
| DE | 202007003093 U1 | 7/2007 |
| EP | 568383 A1 | 11/1993 |
| EP | 0621009 | 4/1994 |
| EP | 646358 A1 | 4/1995 |
| EP | 0776231 B1 | 6/1997 |
| EP | 950376 | 10/1999 |
| EP | 0966924 A1 | 12/1999 |
| EP | 0996925 A1 | 5/2000 |
| EP | 1219251 A1 | 7/2002 |
| EP | 1219252 A1 | 7/2002 |
| EP | 1219253 A1 | 7/2002 |
| EP | 1350476 | 10/2003 |
| EP | 1621139 A2 | 2/2006 |

(56) References Cited

FOREIGN PATENT DOCUMENTS

| | | |
|---|---|---|
| EP | 1731105 A1 | 12/2006 |
| FR | 2710270 A1 | 3/1995 |
| JP | 2000033089 A | 2/2000 |
| JP | 2006320750 | 11/2006 |
| WO | WO-9426175 A1 | 11/1994 |
| WO | WO-9608208 A1 | 3/1996 |
| WO | WO-9608897 A1 | 3/1996 |
| WO | WO-9712557 A1 | 4/1997 |
| WO | WO-9729709 A1 | 8/1997 |
| WO | WO-9735521 A1 | 10/1997 |
| WO | WO-9810712 A1 | 3/1998 |
| WO | WO-9903536 A1 | 1/1999 |
| WO | WO-0030592 A1 | 6/2000 |
| WO | WO-0032253 A1 | 6/2000 |
| WO | WO-0217810 A2 | 3/2002 |
| WO | WO-0239890 A2 | 5/2002 |
| WO | WO-0239918 A1 | 5/2002 |
| WO | WO-02058543 A2 | 8/2002 |
| WO | WO-02094133 A1 | 11/2002 |
| WO | WO-03005890 A2 | 1/2003 |
| WO | WO-03067341 A2 | 8/2003 |
| WO | WO-03077730 A2 | 9/2003 |
| WO | WO-03091839 A2 | 11/2003 |
| WO | WO-2005087112 A1 | 9/2005 |
| WO | WO-2005094432 A2 | 10/2005 |
| WO | WO-2006110733 A2 | 10/2006 |
| WO | WO-2007119232 A2 | 10/2007 |
| WO | WO-2008012787 A2 | 1/2008 |
| WO | WO-2008024502 A2 | 2/2008 |
| WO | WO-2009073577 A2 | 6/2009 |
| WO | WO-2010030114 A2 | 3/2010 |

OTHER PUBLICATIONS

U.S. Appl. No. 12/399,482, filed Mar. 6, 2009 entitled Methods and Devices for Providing Access Into a Body Cavity.
U.S. Appl. No. 12/399,547, filed Mar. 6, 2009 entitled Surgical Access Devices and Methods Providing Seal Movement in Predefined Paths.
U.S. Appl. No. 12/399,625, filed Mar. 6, 2009 entitled Methods and Devices for Providing Access Into a Body Cavity.
U.S. Appl. No. 12/399,633, filed Mar. 6, 2009 entitled Methods and Devices for Providing Access Into a Body Cavity.
U.S. Appl. No. 12/399,656, filed Mar. 6, 2009 entitled Surgical Access Devices and Methods Providing Seal Movement in Predefined Movement Regions.
U.S. Appl. No. 12/512,542, filed Jul. 30, 2009 entitled Methods and Devices for Providing Access Into a Body Cavity.
U.S. Appl. No. 12/512,568, filed Jul. 30, 2009 entitled Methods and Devices for Providing Access Into a Body Cavity.
U.S. Appl. No. 12/766,086, filed Apr. 23, 2010 entitled Methods and Devices for Accessing a Body Cavity.
"Applied GelPort System" by Applied Medical Resources Corporation (2004).
"Bard® Bi-Directional and Kelly-Wick Tunnelers—Instructions for Use," by Bard Peripheral Vascular (Apr. 2006).
"Intrack XT—Low Profile Atraumatic Clamps," by Novare Surgical Systems, Inc. (2002).
"1 Lap Disc Hand Access Device—Ref. Ld111," by Ethicon Endo-Surgery, Inc. (date unknown but no later than May 15, 2007, date of citation in U.S. Appl. No. 11/398,985; 1 page).
"Adult Cardiac Surgical Instruments," from the website of Genesee BioMedical, Inc. (date of first publication unknown; downloaded May 3, 2007; 4 pages).
"Applied GelPort Advanced Access Device," by Applied Medical Resources Corporation (Nov. 2002).
"Hand Instruments," from the website of Olympus Surgical America (date of first publication unknown; downloaded May 3, 2007; 4 pages).
"Pen Competitors," (date of first publication unknown but no later than May 15, 2007, date of citation in U.S. Appl. No. 11/398,985; 1 page).
Advanced Surgical Concepts (ASC), 510(k) TriPort Laparoscopic Access Device, Dec. 26, 2007, 8 pages.
Ashida, R. et al., "Indocyanine Green is an Ideal Dye for Endoscopic Ultrasound-Guided Fine-Needle Tattooing of Pancreatic Tumors" *Endoscopy*, 38, pp. 190-192 (2006).
Desai, M. et al., "Laprascopic and Robtoic Urology: Scarless single port transumbilical nephrectomy and pyeloplasty: first clinical report," Journal Compilation, 2008 BJU International, 101, 83-88.
http://www.innomedic.de/en/products/innomotion_overview.php (Innomedic Products), accessed Oct. 24, 2006.
http://www.intuitivesurgical.com/products/index.aspx (Intuitive Surgical Products), accessed Oct. 24, 2006.
http://www.lap-laser.com/e/laser_m/prod/med.html (LAP Laser Application), accessed Oct. 24, 2006.
Ideas for Surgery.com, "Surgeon performs single-port laparoscopic surgery," dated Dec. 1, 2007.
Lee, D.I. et al., "Novel Approach to Minimizing Trocar Sites during Challenging Hand-Assisted Laparoscopic Surgery Utilizing the Gelport: Trans-Gel Instrument Insertion and Utilization," *Journal of Endourology*, vol. 17, No. 2, pp. 69-71 (Mar. 2003).
Maurin, et al., "A new robotic system for CT-guided percutaneous procedures with haptic feedback," LSIIT (UMR CNRS-ULP 7005), Louis Pasteur University, Bd. S. Brant, BP 10413, Strasbourg Illkirch 67412, France.
Maurin, et al., "A Parallel 5 DOF Positioner for Semi-Spherical Workspaces", Proceedings of DETC'04, ASME 2004 Design Engineering Technical Conferences and Computers and Information in Engineering Conference, Sep. 28-Oct. 2, 2004, Salt Lake City Utah USA.
Maurin, et al., "A Parallel Robotic System with Force Sensors for Percutaneous Procedures Under CT-Guidance", LSIIT (UMR CNRS-ULP 7005), Strasbourg I University Bd. S. Brant, BP 10413, 67412 Illkirch cedex, France.
Stoianovici, et al., "A Novel Mechanical Transmission Applied to Percutaneous Renal Access", DSC—vol. 61, Proceedings of the ASME Dynamic Systems and Control Division 1997.
Twentieth Edition—Illustrations of Surgical Instruments, by The Kny-Scheerer Company, New York, USA, pp. 1003, 1026, 1028-1029, 1133, 2034, 2068-2069, 2097-2099, 2132, 2137, 2144, 2155-2156, 2162, 2167-2171, 2173, 2175, 2244, 2255, 2281-2282, 2327, 2333, 2338-2348, 2352, 2355, 2359, 2371, 3017, 3039-3073, 3132, 3165, 3168-3169, 3208-3209, 3219 (Jul. 1915).
URobitics, Brady Urological Institute, Johns Hopkins Medical Institutions, "Z-Stage PAKY", date of publication unknown but no later than Oct. 26, 2006 (date of citation in U.S. Appl. No. 11/307,231).
URobotics, Brady Urological Institute, Johns Hopkins Medical Institutions, "PAKY Needle Driver," date of publication unknown but no later than Oct. 26, 2006 (date of citation in U.S. Appl. No. 11/307,231).
URobotics, Brady Urological Institute, Johns Hopkins Medical Institutions, "The RCM Robot", date of publication unknown but no later than Oct. 26, 2006 (date of citation in U.S. Appl. No. 11/307,231).
Webpage of Novare Surgical, Inc. featuring clamps (date of first publication unknown; downloaded Feb. 23, 2004; 1 page).
International Preliminary Report on Patentability issued in International Application No. PCT/US2011/035525 issued Nov. 13, 2012.
International Preliminary Report on Patentability issued in International Application No. PCT/US2011/035526 issued Nov. 13, 2012.
International Search Report and Written Opinion issued in International Application No. PCT/US2011/035525 issued Aug. 19, 2011.
International Search Report issued in International Application No. PCT/US2011/035511 dated Oct. 10, 2011.
International Search Report issued in International Application No. PCT/US2011/035526 issued Aug. 19, 2011.
Written Opinion issued in International Application No. PCT/US2011/035526 issued Aug. 19, 2011.

\* cited by examiner

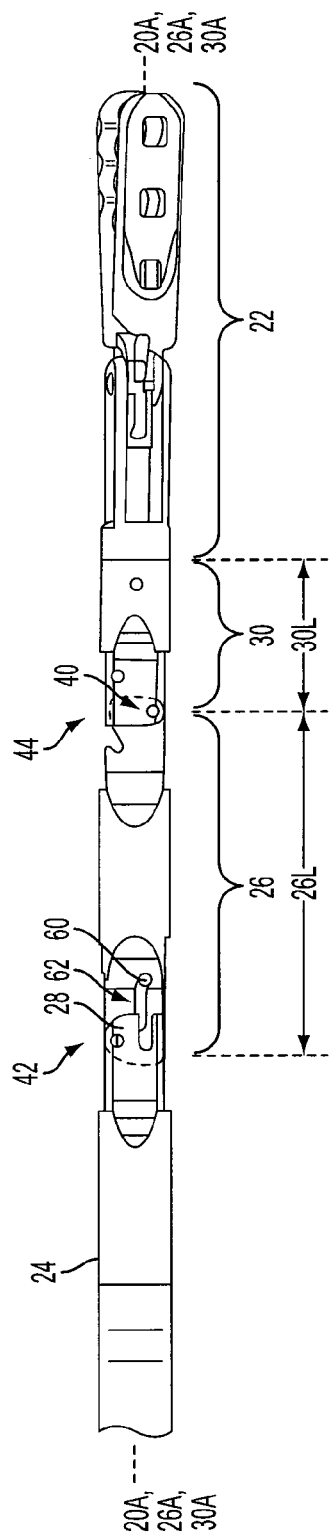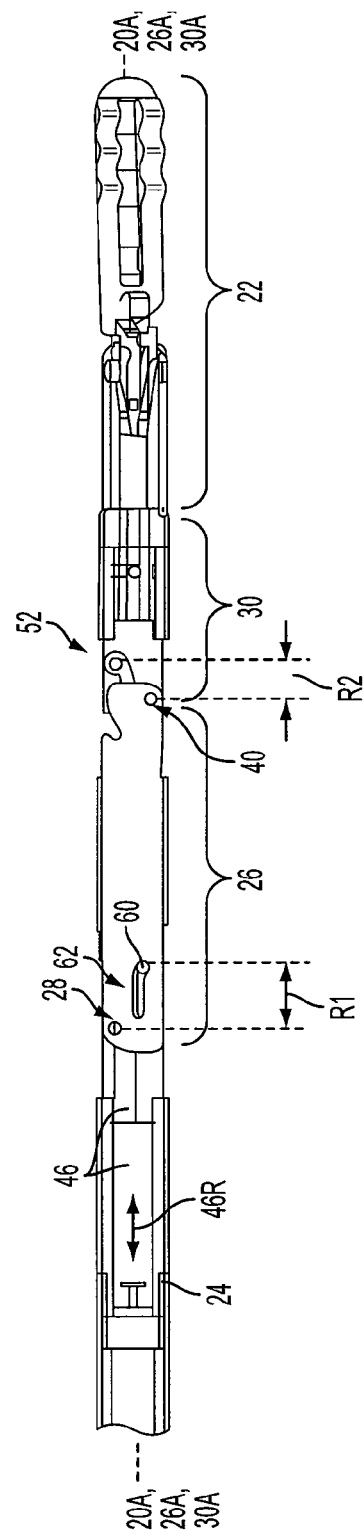

LAPAROSCOPIC DEVICE WITH COMPOUND ANGULATION

CROSS REFERENCE TO RELATED APPLICATIONS

The present application claims priority to U.S. Provisional Application No. 61/249,780 filed on Oct. 8, 2009 and entitled "Articulatable Laparoscopic Tools," which is hereby incorporated by reference in its entirety.

FIELD OF THE INVENTION

The present invention relates to methods and devices for performing minimally invasive surgical procedures.

BACKGROUND OF THE INVENTION

Many surgical procedures involve inserting various instruments through the working channel of a surgical access device. The instruments are used to view, engage, and/or treat tissue within a body cavity or other surgical site to achieve a diagnostic or therapeutic effect. In laparoscopic abdominal procedures for example, the abdominal cavity is generally insufflated with $CO_2$ gas to a pressure of around 15 mm Hg. The abdominal wall is pierced and a plurality of tubular cannulas, each defining a working channel, are inserted at various points into the abdominal cavity. A laparoscopic telescope connected to an operating room monitor can be used to visualize the operative field and can be placed through one of the cannulas. Other laparoscopic instruments such as graspers, dissectors, scissors, retractors, etc. can be placed through the other cannula(s) to facilitate various manipulations by the surgeon. In this type of procedure, because of the positioning of the cannulas, it can be relatively easy to "triangulate" the tips of two separate instruments, e.g., bring the tips together at a single point within the abdominal cavity. For example, a first instrument could be passed through a cannula in the left side of the patient's abdomen and operated with the surgeon's left hand while a second instrument could be passed through another cannula in the right side of the patient's abdomen and operated with the surgeon's right hand. The surgeon can then easily bring the tips of the two instruments together at an internal point, e.g. in the center of the patient's abdomen. A laparoscope viewing instrument can also be passed through a third cannula, positioned for example in the center of the patient's abdomen, such that the tips of the two instruments can be easily visualized from above.

In other surgical procedures, however, visualization and triangulation is not as straightforward. For example, in Single Incision Laparoscopic Surgery (SILS) or Single Site Laparoscopic Surgery (SSLS), a single laparoscopic entry point is formed, e.g., through the navel. An access device having one or more working channels, and typically a plurality of working channels, is then installed in the entry point and all instruments required for performing the surgery are inserted through this same access device. In such procedures, the elongate shafts of the various instruments end up being generally parallel to one another while inserted through the access device. This can make it very difficult to triangulate the tips of two instruments within the abdominal cavity, especially if the instruments do not have distal articulation capabilities. In addition, since the viewing scope is inserted generally along the same axis as the various other instruments, it can be difficult or impossible to see the tips of the instruments. Furthermore, the handles of the various instruments often end up being positioned in close proximity to one another and create a so-called "chopstick" effect, which describes interference between the surgeon's hands, between the surgeon's hands and the instruments, and between the instruments. Interference between the handles and/or the positioning of the handles can limit maneuverability and/or lead to discomfort for the surgeon. These problems can unduly lengthen the duration of the surgery, potentially increasing the risk of patient complications. Also, in cases where it is impossible to achieve adequate triangulation and/or visualization, a second or even third entry point must be formed, increasing trauma to the patient and creating additional scars.

Even in multiple-incision procedures or where triangulation and visualization is possible (e.g., where one or more of the devices includes a distal articulation capability), triangulation, visualization, comfort, and maneuverability can still be sub-optimal.

Accordingly, there is a need for methods and devices which allow laparoscopic procedures to be performed with an enhanced ability to triangulate and visualize surgical instruments and with improved surgeon comfort and instrument maneuverability.

SUMMARY OF THE INVENTION

The present invention generally provides methods and devices for performing minimally invasive surgical procedures. In one embodiment, an articulating laparoscopic device is provided that includes an elongate shaft having first and second articulation joints such that the shaft is configured to form compound angles, an end effector coupled to a distal end of the elongate shaft and positioned distal of the first and second articulation joints, and an articulator element extending through the elongate shaft and configured to rigidly maintain the elongate shaft in a plurality of positions in which the elongate shaft has compound angles.

The articulator element can have a variety of configurations, and in one exemplary embodiment the articulator element can be rigid. At least a portion of the articulator element can translate longitudinally relative to the elongate shaft, and at least a portion of the articulator element can translate laterally relative to the elongate shaft. The articulator element can include a plurality of sections, such as first and second articulation rods extending through the elongate shaft and being pivotally coupled to one another at a pivot point. The pivot point can float laterally relative to the elongate shaft. The articulator element can also include a pin that extends into a cam slot formed in a portion of the elongate shaft for guiding movement of the articulator element relative to the elongate shaft.

The elongate shaft can also have a variety of configurations. In one exemplary embodiment, the second articulation joint can be movable toward and away from a longitudinal axis of the elongate shaft, and the first articulation joint can be limited to longitudinal movement along an axis substantially parallel to the longitudinal axis of the elongate shaft. The elongate shaft can include a plurality of sections, such as a main shaft extending from a handle, a first linkage having a proximal end coupled to a distal end of the main shaft at the first articulation joint, and a second linkage having a proximal end coupled to a distal end of the first linkage at the second articulation joint. The first and second linkages can be movable between an initial position in which the first and second linkages are longitudinally aligned with the longitudinal axis of the elongate shaft and an articulated position in which the first and second linkages are angularly oriented relative to the longitudinal axis of the elongate shaft.

Although the device can include any type of end effector, in one embodiment, the end effector can include graspers having opposed jaws. The elongate shaft can include a flexible actuator element extending therethrough and being effective to move the opposed jaws between a closed position and an open position.

In another embodiment, an articulating laparoscopic device is provided that includes an elongate shaft, a first linkage coupled to a distal end of the elongate shaft at a first articulation joint, a second linkage coupled to a distal end of the first linkage at a second articulation joint, and an articulator element having a proximal articulation rod extending through the elongate shaft and a distal articulation rod extending through the first linkage. A proximal end of the distal articulation rod can be pivotally coupled to a distal end of the proximal articulation rod at a pivot point that floats laterally relative to the elongate shaft and the first linkage, and a distal end of the distal articulation rod can be coupled to the second linkage.

The proximal and distal articulation rods can vary in any number of ways. In an exemplary embodiment, the proximal and distal articulation rods are rigid. The proximal articulation rod can be configured to translate longitudinally relative to the elongate shaft and the distal articulation rod can be configured to translate laterally relative to the first linkage. The proximal articulation rod can include a pin that extends into a cam slot formed in the first linkage.

The device can include an end effector coupled to a distal end of the second linkage. The end effector can have a variety of configurations, such as being opposed jaws. The device can include an actuator element configured to move the opposed jaws between a closed position and an open position. While the actuator element can also have a variety of configurations, in one embodiment, the actuator element can extend through the elongate shaft, the first linkage, and the second linkage and be coupled to a proximal end of the opposed jaws.

In another embodiment, an articulating laparoscopic device is provided that includes an elongate shaft, a first linkage having a proximal end coupled to a distal end of the elongate shaft at a first articulation joint, a second linkage having a proximal end coupled to a distal end of the first linkage at a second articulation joint, an end effector coupled to a distal end of the second linkage, and a rigid articulator element having a proximal portion disposed within the elongate shaft and configured to translate longitudinally relative to the elongate shaft, and a distal portion disposed within the first linkage and configured to translate laterally relative to the first linkage. The second articulation joint is movable toward and away from a longitudinal axis of the elongate shaft such that the first and second linkages are movable between an initial position in which the first and second linkages are longitudinally aligned with the longitudinal axis of the elongate shaft and an articulated position in which the first and second linkages are angularly oriented relative to the longitudinal axis of the elongate shaft.

While the articulator element can have a variety of configurations, in an exemplary embodiment, the articulator element can be configured to rigidly maintain the first and second linkages in a fixed angular orientation through an entire range of motion of the first and second linkages between the initial and articulated positions. The proximal portion of the articulator element can be coupled to the distal portion of the articulator element at a pivot point that is movable laterally relative to the elongate shaft and the first linkage.

BRIEF DESCRIPTION OF THE DRAWINGS

The invention will be more fully understood from the following detailed description taken in conjunction with the accompanying drawings, in which:

FIG. 4 is a partial, side view of a distal portion of the shaft of FIG. 1;

FIG. 5 is a cross-sectional view of the distal portion of the shaft of FIG. 4;

DETAILED DESCRIPTION OF THE INVENTION

Figure 1:
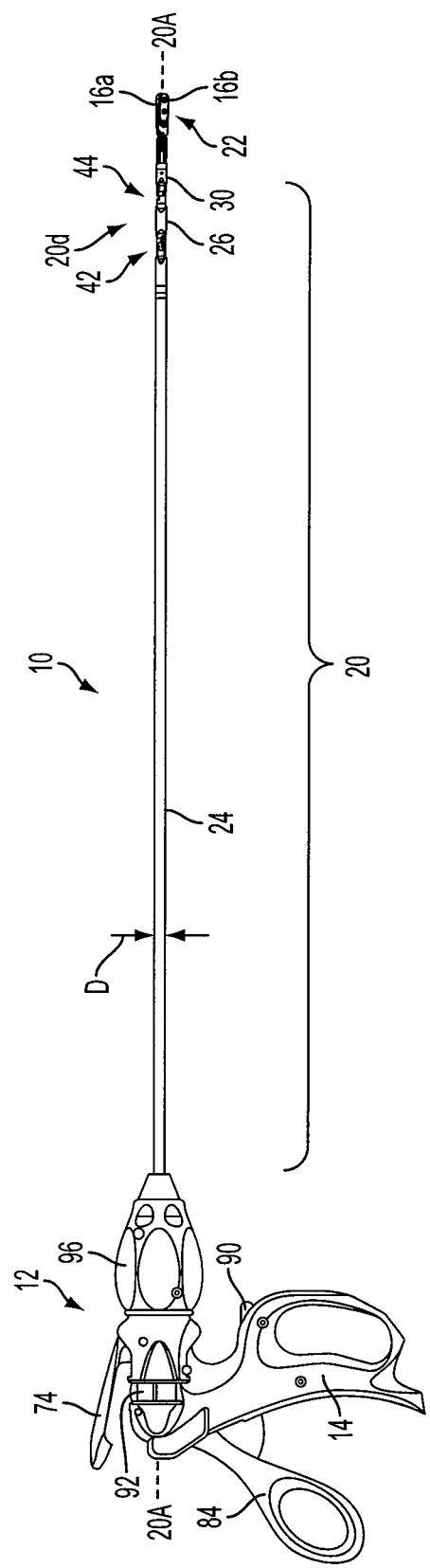
FIG. 1 is a side view of a laparoscopic device including a handle and an articulatable shaft extending distally from the handle, the shaft being in a straight configuration and having an end effector coupled to a distal end thereof.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary devices and methods are provided for performing minimally invasive surgical procedures. In general, the devices and methods allow a shaft of a surgical instrument to form a compound angle, thereby facilitating optimal positioning of a working distal end of the instrument relative to a surgical site. In an exemplary embodiment, a laparoscopic device includes an elongate shaft having a distal portion configured to be movable between a first configuration in which the distal portion of the shaft is substantially straight or linear and a second configuration in which the distal portion of the shaft is bent at a compound angle. The shaft's distal portion can be configured to be articulated in a wide range of compound angles, and it can be configured to be selectively locked in a fixed position anywhere within that range, thereby allowing the device to be easily held in a desired bent position. The device can thus be inserted into a patient's body with the shaft in the first configuration, and it can be subsequently manipulated to move the shaft from the first configuration to the second configuration to allow the device's working distal end, e.g., an end effector, to be optimally angled within the body relative to a surgical site and/or any other surgical instruments at the surgical site. The shaft can also be configured to move from the second configuration to the first configuration to ease removal of the device from the patient. Such a configuration can be particularly advantageous where two or more instruments are inserted into a patient's body cavity through the same entry port in tissue because it can allow for triangulation. In particular, distal tips of the instruments can be brought together at a single point within the body cavity, even though the instruments' shafts extend generally parallel to one another.

A person skilled in the art will appreciate that while the methods and devices are described in connection with laparoscopic procedures in which one or more surgical instruments are inserted into a patient's body through an artificial opening, e.g., an incision, the methods and devices disclosed herein can be used in numerous surgical procedures and with numerous surgical instruments. By way of non-limiting example, the methods and devices can be used in open surgical procedures.

A person skilled in the art will also appreciate that the devices disclosed herein can be inserted into a body in any way, such as through a natural orifice, through an incision or puncture hole formed in tissue, etc. The devices can be inserted directly into a patient's body or can be inserted through an access device having a working channel through which a shaft of a surgical instrument can be advanced. A person skilled in the art will further appreciate that an access device can be configured to allow insertion of a single surgical instrument therethrough, such as with a straight cannula, or to allow simultaneous insertion of multiple instruments therethrough, such as with a surgical access device having multiple sealing ports each defining a working channel. Devices disclosed herein can alternatively or additionally be introduced into a body through an auxiliary passageway along the outside of a scoping device or other surgical instrument, as will be appreciated by a person skilled in the art. Exemplary embodiments of a surgical instrument that provides such an auxiliary passageway are described in more detail in U.S. Pat. No. 7,615,005 issued Nov. 10, 2009 entitled "Medical Apparatus For Use With An Endoscope," which is hereby incorporated by reference in its entirety.

In an exemplary embodiment, shown in FIG. 1, a surgical device 10 is provided that includes a proximal handle 12 having an elongated, tubular shaft 20 extending distally therefrom. The shaft 20 can have a working element or end effector 22, generally referred to as an "end effector," at a distal end thereof. The end effector 22 in the illustrated embodiment includes a tissue grasper having a pair of opposed jaws 16a, 16b configured to move between open and closed positions, but as will be appreciated by a person skilled in the art, the end effector 22 can include any tool, e.g., a grasper, a dissector, scissors, forceps, a retractor, a light, etc. As discussed further below, the handle 12 can be configured to operate the end effector 22 and to articulate and/or rotate the shaft 20.

Figure 2:
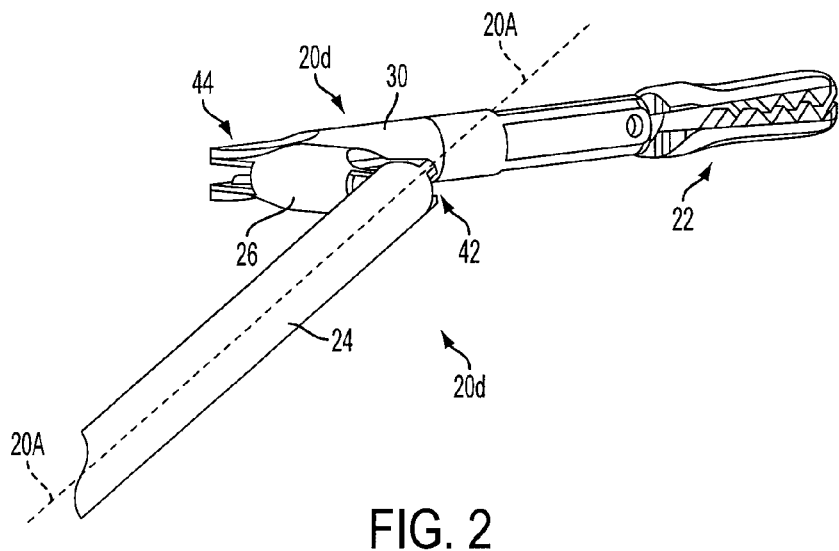
FIG. 2 is a perspective view of a distal portion of the shaft of FIG. 1 showing the shaft in an articulated configuration.

Generally, the shaft 20 can be configured to be movable between a linear or straight configuration, generally referred to as a "straight configuration," in which the shaft 20 extends substantially along a longitudinal axis 20A thereof, as illustrated in FIG. 1, and an articulated, bent, or compound angle configuration, generally referred to as an "articulated configuration," in which portions of the shaft 20 do not extend parallel to the longitudinal axis 20A. In the illustrated exemplary embodiment, the shaft 20 is not biased to either the straight configuration or the articulated configuration, although as will be appreciated by a person skilled in the art, the shaft 20 can be biased to one of the configurations, e.g., using a bias spring. Although any portion of the shaft 20 can be articulated or bent to misalign the shaft 20 from its longitudinal axis 20A, in an exemplary embodiment, as shown in FIG. 2, a distal portion 20d of the shaft 20 can be configured to articulate to form a compound angle. Although the shaft 20 can be configured to bend any number of times to form a compound angle, the shaft 20, as in the illustrated embodiment, can be articulated at first and second articulation joints 42, 44 to form a triangulated compound angle, as discussed in further detail below.

Figure 3:
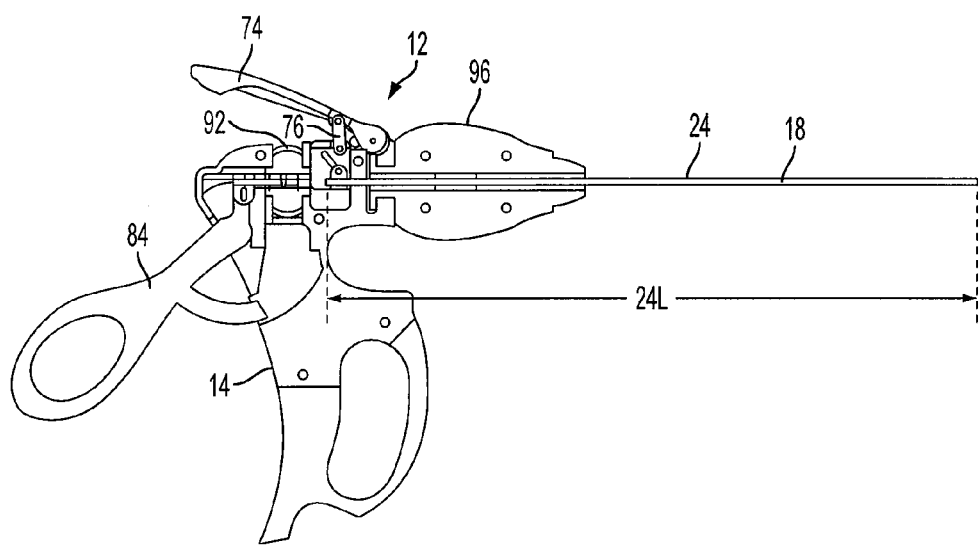
FIG. 3 is a partial, side cross-sectional view of the device of FIG. 1.

The shaft 20 can have a variety of sizes, shapes, and configurations. The shaft 20 can be rigid, flexible, or a combination thereof, but in an exemplary embodiment it is rigid, e.g., made from a generally non-bendable material such as a hard polymer or titanium. Portions of the shaft 20 can be less flexible or more rigid than a remainder of the shaft 20 to facilitate insertion through tissue and/or operation of the end effector 22. As mentioned above, the shaft 20 can be tubular, and it can have an inner lumen 18 extending through at least a proximal portion thereof, as shown in FIG. 3.

The shaft 20 can have any longitudinal length, although in an exemplary embodiment it is long enough to allow the handle 12 to be manipulated outside a patient's body when the shaft 20 extends through an opening in the body with the end effector 22 disposed within a body cavity. In this way, the shaft 20 and the end effector 22 can be easily manipulated when the device 10 is in use during a surgical procedure. The shaft 20 can have any diameter D, e.g., less than or equal to about 10 mm, and more particularly less than or equal to about 5 mm, to allow for insertion of the shaft 20 through an access device, such as during a laparoscopic surgical procedure. The end effector 22 mated to the shaft's distal end can have a diameter equal to or less than the shaft's diameter D, at least when the jaws 16a, 16b are in a closed position, to further facilitate insertion of the device's distal portion into a patient's body.

Figure 8:
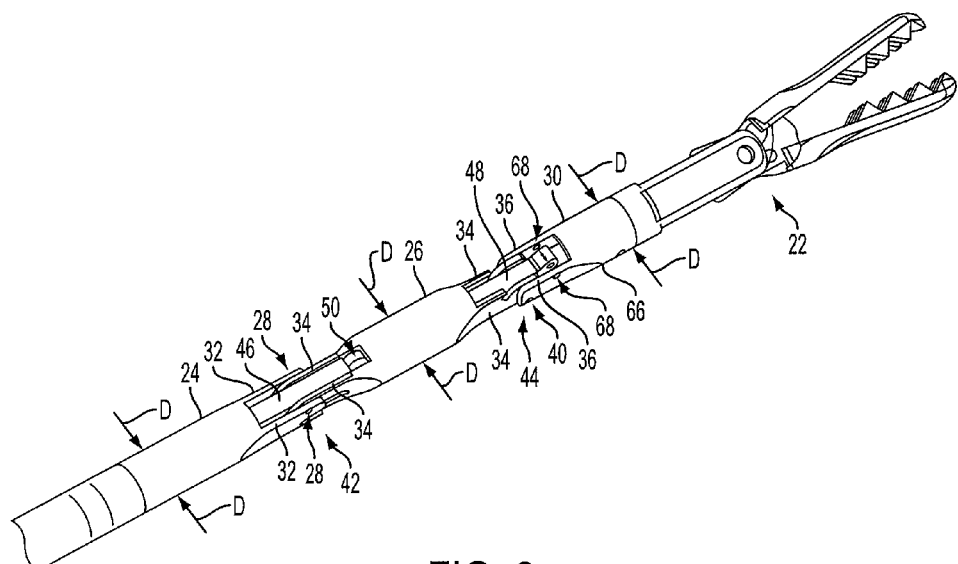
FIG. 8 is a perspective view of the distal portion of the shaft of FIG. 4.

In an exemplary embodiment, the shaft 20 can be substantially cylindrical to help the shaft 20 pass smoothly into a body. The shaft 20 can have any constant or varying shape along its longitudinal length, and the shaft's diameter D can be uniform or non-uniform along its longitudinal length. In an exemplary embodiment, as shown in FIGS. 1 and 8, the shaft 20 can have a substantially uniform diameter D along its longitudinal length except at one or both of the articulation joints 42, 44, which can have diameters that differ from the shaft's diameter D, as discussed further below.

The shaft 20 can include a plurality of sections, segments, or linkages, generally referred to as "linkages," along the shaft's longitudinal length to facilitate articulation of the shaft 20. As shown in the embodiment illustrated in FIGS.

1, 2, and 4-8, the shaft 20 can include a proximal elongate shaft 24, a first linkage 26 coupled to a distal end of the proximal shaft 24, and a second linkage 30 coupled to a distal end of the first linkage 30. While two shaft linkages are illustrated in FIGS. 1, 2, and 4-8, a person skilled in the art will appreciate that in other embodiments, the shaft can include any number of linkages.

The proximal shaft 24 and the linkages 26, 30 can have a variety of sizes, shapes, and configurations. For example, the proximal shaft 24 and the linkages 26, 30 can each be in the form of a relatively rigid tubular section with the inner lumen 18 extending therethrough. As in the illustrated embodiment, the proximal shaft 24 can have a longer longitudinal length 24L than the two linkages 26, 30 alone or together. Also as in the illustrated embodiment, a longitudinal length 26L of the first linkage 26 can be longer than a longitudinal length 30L of the second linkage 30. Alternatively, the longitudinal length 30L of the second linkage 30 can be larger than the longitudinal length 26L of the first linkage 26, or the first and second linkages 26, 30 can have substantially equal longitudinal lengths 26L, 30L. As shown in FIG. 3, a proximal portion of the proximal shaft 24 can be disposed within the handle 12 with a remainder of the proximal shaft 24 extending distally from the handle 12. As shown in FIGS. 1 and 2, the proximal shaft 24 can extend distally from the handle 12 in a generally straight line along the shaft's longitudinal axis 20A. In other exemplary embodiments, the proximal shaft 24 can have a bend or curvature near its proximal end, such as is illustrated in another exemplary embodiment of a laparoscopic device 10' in FIG. 11. Such a bend or curvature can be helpful in preventing handles of two instruments from interfering with the other when two or more instruments are inserted in closely-spaced instrument openings or closely spaced trocars. As will be appreciated by a person skilled in the art, a bend or curvature in the proximal portion of the proximal shaft 24 can be fixed, or alternatively, it can be movable, such as in the form of a flexible "elbow" that can be adjusted, such as manually, at the point of use.

Figure 6:
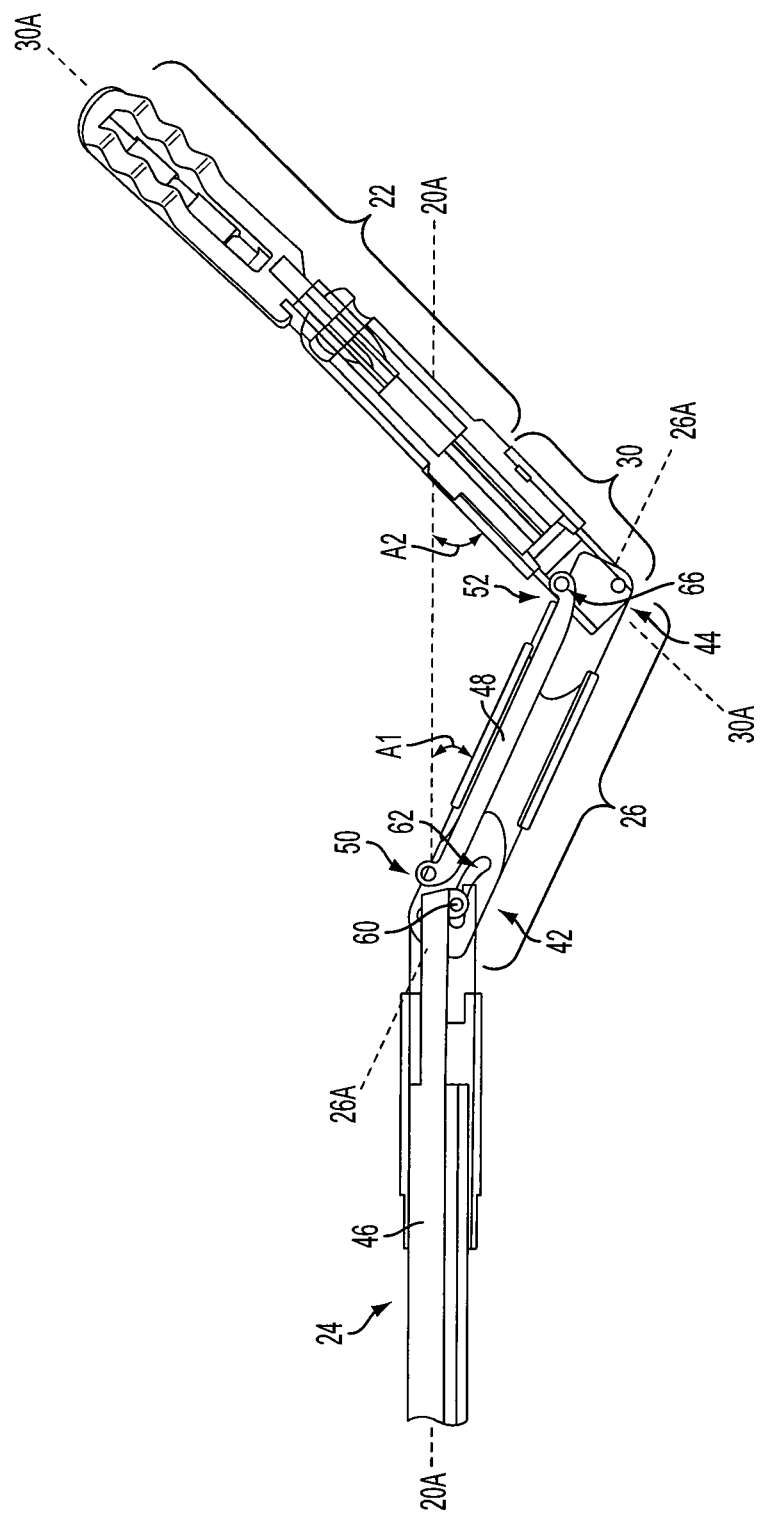
FIG. 6 is a cross-sectional view of the distal portion of the shaft of FIG. 4 showing the shaft in an articulated configuration.
Figure 7:
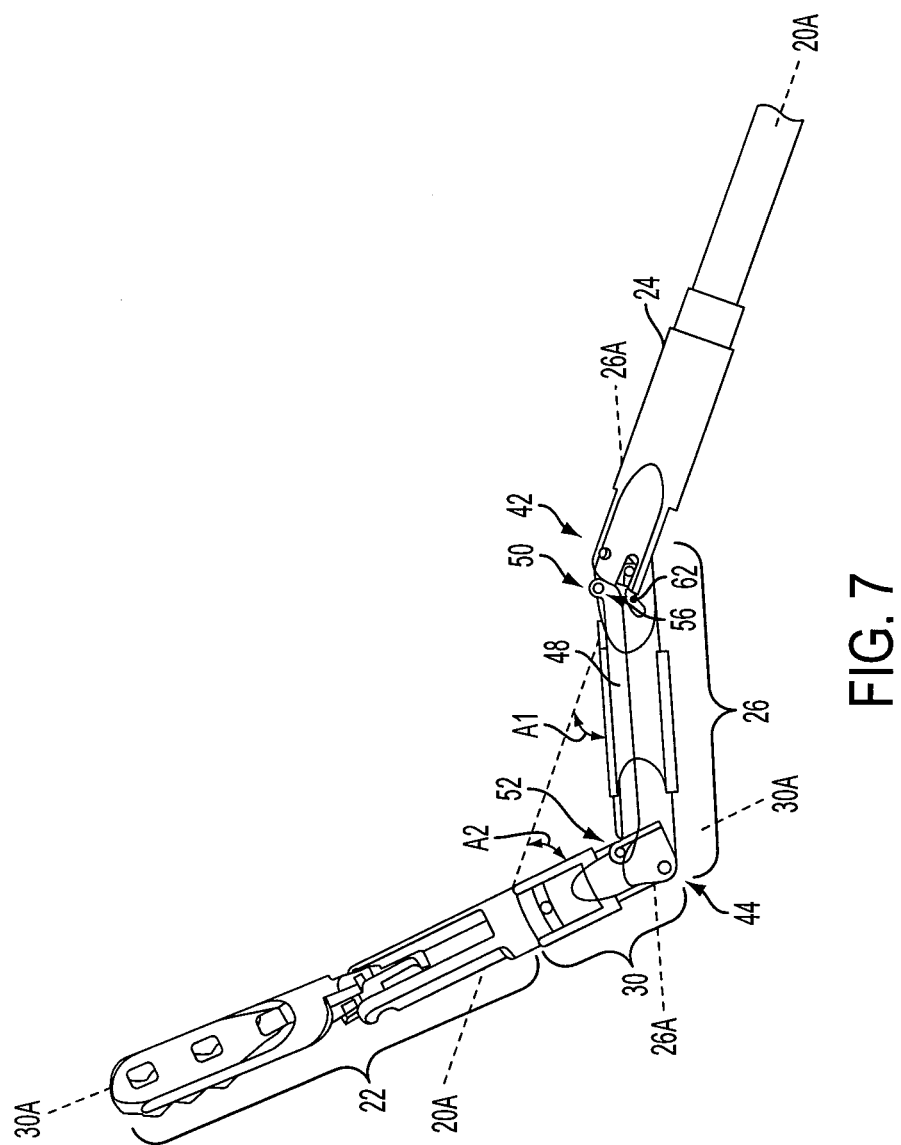
FIG. 7 is another cross-sectional view of the distal portion of the shaft of FIG. 4 showing the shaft in an articulated configuration.

The proximal shaft 24 and the linkages 26, 30 can be configured to facilitate smooth and controlled articulation of the shaft 20 relative to the handle 12 with the first articulation joint 42 being located between the proximal shaft 24 and the first linkage 26 to allow the proximal shaft 24 and the first linkage 26 to be angled relative to one another, and with the second articulation joint 44 being located between the first and second linkages 26, 30 to allow the first and second linkages 26, 30 to be angled relative to one another offset from the shaft's axis 20A. The proximal shaft 24 and the linkages 26, 30 can thus be configured to articulate to form a compound angle in the shaft 20. The proximal shaft 24 can be configured to be in a fixed position along the shaft's longitudinal axis 20A when the shaft 20 is in the straight configuration and in the articulated configuration, as shown in FIGS. 1, 2, and 4-8. In contrast, the first and second linkages 26, 30 can be configured to be longitudinally aligned with the shaft's longitudinal axis 20A when the shaft 20 is in the straight configuration, as shown in FIGS. 1, 4, 5, and 8, and the first and second linkages 26, 30 can be angularly oriented relative to the shaft's longitudinal axis 20A when the shaft 20 is in the articulated configuration, as shown in FIGS. 2, 6, and 7. As mentioned above, the end effector 22 can be mated to a distal end of the shaft 20, and in particular the distal end of the second linkage 30, such that the end effector 22 is positioned distal to the articulation joints 42, 44. This can allow the end effector 22 to articulate with the second linkage 30 and thereby be angularly oriented relative to the shaft's longitudinal axis 20A in coordination with the second linkage 30, as illustrated in FIGS. 2, 6, and 7. In this way, the shaft 20 can be inserted into a patient's body and the distal portion 20d thereof can be articulated inside the body through actuation of the handle 12, as discussed further below, without altering the position of a proximal portion of the shaft 20, e.g., the proximal shaft 24, that extends through an opening in the body, either directly or through an access device. The end effector 22 can thus be oriented to extend toward and in a facing relationship with the longitudinal axis 20A.

The proximal shaft 24 and the linkages 26, 30 can be coupled together in a variety of ways. As in the illustrated embodiment, a proximal end of the proximal shaft 24 can be fixedly or rotatably coupled to the handle 12, and a distal end of the proximal shaft 24 can be pivotably coupled to a proximal end of the first linkage 26 at a first pivot point to partially form the first articulation joint 42. The first linkage 26 can thereby be configured to articulate or rotate, as shown in FIG. 7, relative to the proximal shaft 24 about the first pivot point. The first pivot point can have an axis that is generally perpendicular to the longitudinal axis 20A of the proximal shaft 24. The distal end of the first linkage 26 can thus be free to move radially inward toward and outward away from the shaft's longitudinal axis 20A. The first linkage 26 and the second linkage 30 can also be coupled together in a pivotal relationship at a second pivot point to partially form the second articulation joint 44, with the distal end of the first linkage 26 being coupled to a proximal end of the second linkage 30. The second linkage 30 can thereby be configured to articulate or rotate relative to the first linkage 26 about the second pivot point. The first and second pivot points can each have an axis generally perpendicular to the longitudinal axis 20A of the proximal shaft 24. In this way, the first and second linkages 26, 30 can both articulate in the same plane and generally parallel to one another and the proximal shaft 24, to allow the end effector 22 to intersect or "cross" the shaft's longitudinal axis 20A. In other words, a longitudinal axis 26A of the first linkage 26 and a longitudinal axis 30A of the second linkage 30 and the end effector 22 can be aligned with the longitudinal axis 20A of the proximal shaft 24 when the shaft 20 is in the straight configuration, as shown in FIGS. 4 and 5. When the shaft 20 is in the articulated configuration, the longitudinal axes 26A, 30A of the first and second linkages 26, 30 can be transverse to the proximal shaft's longitudinal axis 20A, at first and second angles A1, A2, respectively, as shown in FIGS. 6 and 7, to angularly orient the end effector 22.

The proximal shaft 24 and the linkages 26, 30 can be pivotally coupled together in any way at their associated ones of the first and second pivot points, as will be appreciated by a person skilled in the art. As shown in the illustrated embodiment in FIG. 8, the coupled ends of the proximal shaft 24 and the linkages 26, 30 can be shaped to include respective first, second, and third pairs of spaced arms or devises 32, 34, 36, generally referred to as "arms," for respectively forming the first and second articulation joints 42, 44 between the adjacent proximal shaft 24 and first linkage 26 and the adjacent first and second linkages 26, 30. The diameter D of the shaft 20 at the arms 32, 34, 36 can be less than the diameter D of a remainder of the shaft 20, which can help facilitate articulation at the joints 42, 44, as discussed further below. As shown in the embodiment illustrated in FIG. 8, gaps between the second arms 34 formed on the proximal and distal ends of the first linkage 26 can be less than a gap between the first arms 32 formed on the distal end of the proximal shaft 24 and a gap between the third arms 36 formed on the proximal end of the second linkage 30 to allow the proximal and distal pairs of second arms 34 to be respectively inserted between the first and third arms 32, 36.

The arms 32, 34, 36 can be pivotally connected together in a variety of ways to movably couple the proximal shaft 24 and the linkages 26, 30, as will be appreciated by a person skilled in the art. As in the illustrated embodiment shown in FIGS. 4, 5, 8, and 9, pins (not shown) can be inserted, e.g., by press fit, through respective holes 28 formed in each set of nested first and second arms 32, 34 to form a pivot hinge-type joint located at the first articulation joint 42 between the proximal shaft 24 and first linkage 26. Similarly, pins (not shown) can be inserted through respective holes 40 formed in each set of nested second and third arms 34, 36 to form a pivot hinge-type joint located at the second articulation joint 44 between the first and second linkages 26, 30. The first and second pivot points can be laterally/radially offset from the longitudinal axis 20A of the shaft 20. As in the embodiment shown, the first and second pivot points can be offset from the shaft's central longitudinal axis, which in the illustrated embodiment is shown as the shaft's longitudinal axis 20A, by being positioned near outer edges of the proximal shaft 24 and the linkages 26, 30. The first and second pivot points can be laterally/radially offset from the shaft's central longitudinal axis 20A on opposed sides, as shown in FIGS. 4 and 5. Such opposed edge locations of the first and second pivot points can allow the first and second linkages 26, 30 to pivot in opposite directions, as illustrated in FIGS. 6 and 7. Such an arrangement can also facilitate rotation of the distal portion of first linkage 26 away from the shaft's longitudinal axis 20A and rotation of the proximal portion of the second linkage 30 away from the shaft's longitudinal axis 20A. As shown in FIGS. 6 and 7, such an arrangement can permit the end effector 22, and possibly also the distal portion of second linkage 30 depending on the size of the first and second linkages 26, 30 and on the size of the angles A1, A2, to intersect or "cross" the shaft's longitudinal axis 20A when the shaft 20 is in the articulated configuration.

Although the end effector 22 can be pivotally coupled to the second linkage's distal end such that it can pivot or articulate relative to the second linkage 30, in the illustrated embodiment, a proximal end of the end effector 22 is non-pivotally coupled to a distal end of the second linkage 30, e.g., welded, snapped, or press fit thereon, which can allow the end effector 22 to articulate with the second linkage 30 relative to the first linkage 26, the proximal shaft 24, and the handle 12. The end effector 22 can additionally or alternatively be configured to be movable relative to the second linkage 30, such as by being rotatable relative thereto and/or by opening and closing the jaws 16a, 16b, as discussed further below.

The device 10 can include an articulator element configured to articulate the shaft 20 at the first and second articulation joints 42, 44 to form a compound angle in the shaft 20. The articulator element can have a variety of configurations, but in the illustrated embodiment the articulator element includes a rigid element extending through the shaft 20 configured to move relative thereto to bend the shaft 20 at the articulation joints 42, 44. Having a rigid articulator element can help maximize stability and rigidity of the articulation joints 42, 44 to allow the joints 42, 44 to be fixedly maintained at any angle throughout their range of motion. As shown in FIGS. 5-9, the articulator element can include a multi-bar system including a proximal rigid articulation bar or rod 46, generally referred to as a "rod," extending through the proximal shaft 24, and a distal rigid articulation bar or rod 48, generally referred to as a "rod," extending through the first linkage 26. The proximal and distal rods 46, 48 can be solid or can have one or more hollow portions, same or different from one another. A proximal end (not shown) of the proximal rod 46 can be operatively coupled to an articulation lever 74 at the handle 12, illustrated in FIGS. 1, 3, and 10 and discussed further below. A distal end of the proximal rod 46 can be pivotally coupled to a proximal end of the distal rod 48 at the proximal pivot point 50 to partially form the first articulation joint 42, while a distal end of the distal rod 48 can be pivotally coupled to a proximal end of the second linkage 30 at the distal pivot point 52 to partially form the second articulation joint 44. Although in the illustrated embodiment the proximal rod 46 extends from the handle 12 to the first linkage 26, in some embodiments, an additional rigid rod can couple to the proximal rod's proximal end and extend from the proximal rod's proximal end to the handle 12. Furthermore, as will be appreciated by a person skilled in the art, the additional rigid rod can include multiple rods.

The proximal and distal rods 46, 48 can be pivotally connected together at a proximal pivot point 50 in a variety of ways to movably couple together, as will be appreciated by a person skilled in the art. As in the illustrated embodiment shown in FIGS. 7 and 9, a pin (not shown) can be inserted, e.g., by press fit, through a pivot hole 54 formed in the distal end of the proximal rod 46 and a pivot hole 56 formed in the proximal end of the distal rod 48 to form a pivot hinge-type joint at the proximal pivot point 50 between the proximal and distal rods 46, 48. As in the illustrated embodiment, the proximal pivot point 50 can be a floating pivot point that is not fixed to the first linkage 26. In this way, the proximal pivot point 50 can be laterally movable relative to the first linkage 26 and the proximal shaft 24, e.g., movable toward and away from the first linkage's longitudinal axis 26A and the shaft's longitudinal axis 20A. The gaps between one or both of the first and second arms 32, 34 can provide adequate space for the proximal pivot point 50 to laterally move relative to the proximal shaft 24 and the first linkage 26.

The articulator element can also include at least one pin 60 that extends into at least one corresponding cam track or slot 62, generally referred to as a "slot," formed in a portion of the shaft 20 to guide movement of the proximal pivot point 50 such that the proximal pivot point 50 can remain within an envelope of motion of the shaft 20. In other words, the articulator element can allow the shaft 20 to form a compound angle without any elements of the device 10 extending substantially laterally beyond the diameter D of the shaft 20 or deviating substantially from the shaft's longitudinal axis 20A, or from the linkages' axes 26A, 30A, as shown in the embodiment illustrated in FIGS. 6 and 7. Substantially all of the articulator element, e.g., the proximal and distal rods 46, 48, can thus be contained within the proximal shaft 24 and the linkages 26, 30 throughout the shaft's range of motion, e.g., whether the shaft 20 is in the straight or the articulated configuration. In this way, when the device's distal portion is positioned within a body, the end effector 22 can be angled to approach a surgical site in a non-linear position relative to the proximal shaft 24 while reducing a likelihood of the device 10 having stray parts that could damage surrounding tissue or interfere with nearby instruments.

As in the illustrated embodiment shown in FIGS. 4-7 and 9, the articulator element can include one pin 60 and two slots 62 that slidably receive the pin 60. The slots 62 can have any size and shape configured to slidably mate with the pin 60. In the illustrated embodiment, as shown in FIGS. 4 and 5, the slots 62 have a J-shape with a linear proximal portion and a curved distal portion. The pin 60 can be inserted, e.g., by press fit, into a second hole 64 formed in the distal end of the proximal rod 46 and laterally and longitudinally offset from the proximal rod's hole 54 for pivotal coupling to the distal rod 48. The opposed slots 62 can be formed in the first linkage 26, e.g., formed in each of the first linkage's proximal pair of arms 34. The pin 60 can be positioned at a distal end of the slots 62 when the shaft 20 is in the straight configuration and can be configured to slide proximally within the slots 62 when the proximal rod 46 is actuated to articulate the shaft 20 and move the shaft 20 to the articulated configuration. Similarly, the pin 60 can be configured to slide distally within the slots 62 when the proximal rod 46 is moved distally to move the shaft 20 from the articulated configuration toward the straight configuration. The pin 60 can also be configured to rigidly maintained in any position within the slots 62 and to subsequently move proximally and/or distally within the slots 62 when the shaft 20 is articulated between different angular positions in the articulated configuration, as discussed further below.

As mentioned above, the distal end of the distal rod 48 can be pivotally coupled to the proximal end of the second linkage 30 at the distal pivot point 52, and they can be pivotally coupled together in a variety of ways, as will be appreciated by a person skilled in the art. As in the illustrated embodiment shown in FIGS. 6, 8, and 9, a pin (not shown) can be inserted through respective holes 66, 68 formed in the distal end of the distal rod 48 and the proximal end of the second linkage 30 to form the distal pivot point 52. The distal rod 48 can thus be fixed to the second linkage 30, e.g., be non-floating.

Figure 9:
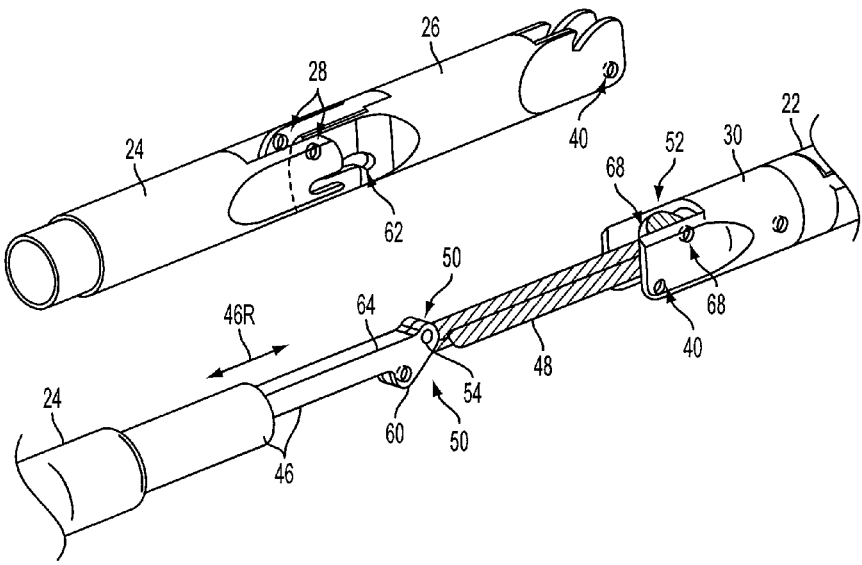
FIG. 9 is an exploded, partial view of a distal portion of the shaft of FIG. 1.
Figure 10:
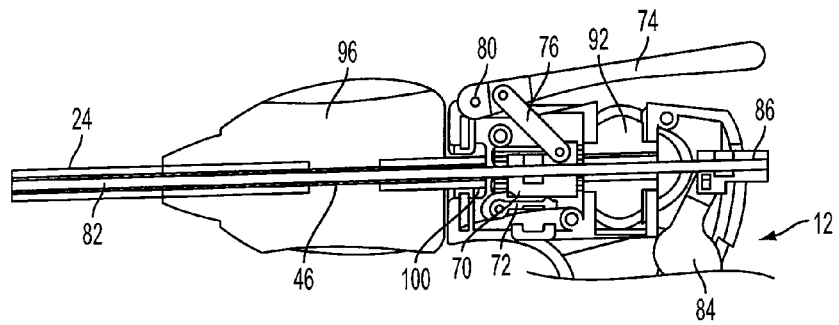
FIG. 10 is a partial, side cross-sectional view of the handle of FIG. 1.

In response to selective movement of the articulation lever 74, the proximal rod 46 can be configured to move longitudinally parallel to the shaft's longitudinal axis 20A in both proximal and distal directions as shown by a double-sided directional arrow 46R in FIGS. 5 and 9. Longitudinal movement of the proximal rod 46 can be configured to impart force or motion to the distal rod 48, thereby causing the shaft 20 to bend at the first and second articulation joints 42, 44. The articulator element can thus be configured to impart a force to the proximal rod 46, e.g., by actuating the articulation lever 74, which transfers force to the distal rod 48, to articulate the shaft 20. In this way, the proximal rod 46 can be configured to translate longitudinally substantially aligned with or parallel to the shaft's longitudinal axis 20A in both proximal and distal directions relative to the shaft 20, while the distal rod 48 can be configured to translate laterally relative to the axis 20A of the shaft 20, both away from and toward the axis 20A, as the shaft 20 bends to form or to be released from a compound angle. Proximal movement of the proximal rod 46 corresponds to movement of the shaft 20 from the straight configuration to the articulated configuration, while distal movement of the proximal rod 46 corresponds to movement of the shaft 20 from the articulated configuration toward the straight configuration. The proximal rod 46 can also be moved proximally and/or distally to move the shaft 20 from one articulated configuration to another articulated configuration, e.g., between different compound angles. The degree of the compound angle formed by the pivoting proximal shaft 24 and linkages 26, 30 can be varied by varying the pulling force on proximal rod 46. Varying the size of the compound angle can change the direction of approach of end effector 22 to an intended site, which can assist in allowing for more precise positioning of the end effector 22. A person skilled in the art will appreciate that the force imparted from the proximal rod 46 to the distal rod 48 can be simultaneous despite the presence of minimal delays in articulation as forces translate along the actuator element.

With the shaft 20 in the articulated configuration, a compound angle is formed, with the axes 20A, 26A, 30A of the proximal shaft 24 and linkages 26, 30 intersecting one another. The axes 20A, 26A, 30A of the proximal shaft 24 and linkages 26, 30 can, however, all lie within a common plane.

FIGS. 4-7 illustrate a compound angle formed by the proximal shaft 24 and the linkages 26, 30, as well as movement of the proximal and distal rods 46, 48 as the proximal shaft 24 and the linkages 26, 30 pivot at the first and second articulation joints 42, 44. As shown in FIG. 5, when the shaft 20 is in the straight configuration, the connection between the proximal rod 46 and the first linkage 26 is spaced from the connection between the proximal shaft 24 and the first linkage 26 by a first distance R1. Likewise, when the shaft 20 is in the straight configuration, the connection between the distal rod 48 and the second linkage 30 is spaced from the connection between the first and second linkages 26, 30 by a second distance R2. As the proximal rod 46 is pulled proximally by a driving force in the handle 12, e.g., by squeezing the articulation lever 74, the proximal rod 46 in turn pulls proximally on the distal rod 48. As the rods 46, 48 are pulled proximally, the rods 46, 48 apply a pulling force on the first and second linkages 26, 30. The opposing, off-center locations of the pivot points between the proximal shaft 24 and the linkages 26, 30, as well as off-center and opposing locations of the pivot connections between the rods 46, 48 and the first and second linkages 26, 30, can result in the first and second linkages 26, 30 pivoting/rotating in opposite directions, relative to the shaft's longitudinal axis 20A, in response to the pulling force of the rods 46, 48, as shown in FIGS. 6 and 7. The first distance R1 dynamically reduces as the rods 46, 48 move proximally and the pin 60 slides proximally in the slots 62.

As shown in FIGS. 6 and 7 and as mentioned above, the pivoting first and second linkages 26, 30 can form a pair of angles A1, A2 when the shaft 20 is in the articulated configuration. The measure of the first and second angles A1, A2 can depend, at least in part, upon the first and second distances R1, R2 between the respective pivot connections, with each of the angles A1, A2 being determined separately by their associated distances R1, R2. A range for the compound angle formed by the first and second angles A1, A2 can be determined by the first and second distances R1, R2, with the distance R2 between the distal pivot connections being less than or equal to the distance R1 between the proximal pivot connections. In one embodiment, the ratio R1/R2 of the separation distances can be the same as the ratio A1/A2 of the angles. The first distance R1 can vary because of the floating proximal pivot point 50 and the sliding of the pin 60 in the slots 62, which can provide for an increased angular range for the first angle A1. The size of the angles A1, A2 can vary, e.g., the first angle A1 can be in a range of about 0° to 45°, and the second angle A2 can be in a range of about 0° to 90°. The first and second linkages 26, 30 being maximally pivoted corresponds to the pin 60 being located as far proximally as possible in the slots 62. Correspondingly, when the angles A1, A2 are each 0° with the shaft 20 in the straight configuration, as shown in FIG. 5, the pin 60 can be positioned at distal-most ends of the slots 62.

As mentioned above, the device 10 can include a handle 12 having controls configured to articulate and rotate the shaft 20 as well as operate the end effector 22. In the embodiment illustrated in FIGS. 1, 3, and 10, the proximal rod 46 is configured in at least a proximal portion thereof as a rigid tube having a proximal end attached to a driver in the handle 12. The driver can have a variety of sizes, shapes, and configurations, but in the illustrated embodiment, the driver includes a carriage 70 having a toothed surface in contact with a pawl 72. The articulation lever 74 extends from a surface of handle 12 and can be manually operated. A connecting rod 76 connects a distal end of the lever 74 to the carriage 70. The lever 74 can pivot about a pin 80 connected at a distal end of the lever 74. The pivoting of the lever 74 can be conveyed through the connecting rod 76 to the carriage 70 to translate the carriage 70 proximally and distally inside the handle 12, and thus proximally and distally longitudinally translate the proximal rod 46 inside the shaft's lumen 18. As the carriage 70 translates, the pawl 72 engages ridges of the toothed surface to hold the proximal rod 46 in a fixed position, and thus also hold the compound angle of the articulated shaft 20 in a fixed position, between actuations of the lever 74. The shaft 20 can thus be rigidly maintained in a plurality of selected, articulated positions, which can ease use of the device 10 and free a surgeon's hand to otherwise manipulate the device 10 or another surgical tool. As the lever 74 pivots downward, the carriage 70 pulls proximal rod 46 proximally within the handle 12, causing the proximal and distal rods 46, 48 to articulate the distal portion of the shaft 20 from the straight configuration to the articulated configuration or from one articulated configuration to another. As the lever 74 pivots upward, the carriage 70 pushes the proximal rod 46 distally, in turn pushing the distal rod 48 distally and moving the first and second linkages 26, 30 of shaft 20 from the articulated configuration toward or entirely to the straight configuration. The lever 74 can be pivoted any amount upward and any amount downward in any order any number of times to optimally angle the shaft 20, with the carriage 70 and the pawl 72 cooperating to lock the shaft 20 at any desired compound angle. A person skilled in the art will appreciate that as an alternative to the lever 74 and the carriage 70, other types of controls can be included within the handle 12 for applying a longitudinal force to the proximal rod 46 parallel to the shaft axis 20A to articulate and/or straighten the shaft 20.

A second driver can be included in handle 12 for operating the end effector 22. The second driver can have a variety of sizes, shapes, and configurations, but as in the illustrated embodiment, it can include a translator element extending from the handle 12, distally through the shaft 20, and to the end effector 22. The translator element can include an actuator, cable, wire, or rod 82, generally referred to as an "actuator," having a proximal end attached to an activator member in the handle 12. The activator member can vary, but as in the illustrated embodiment, it can include a ratchet 86 driven by a thumb trigger 84. The ratchet 86 can be configured to longitudinally translate the actuator 82 parallel to the longitudinal axis 20A of the shaft 20 in response to manual pressure on the trigger 84. As the trigger 84 is pivoted relative to a pistol handle grip 14, the trigger 84 ratchets the actuator 82 proximally or distally through the proximal rod 46. The translator element can also include a flexible segment (not shown) connected to the actuator 82 proximal to the first and second linkages 26, 30, e.g., proximal to the proximal articulation joint 42. The flexible segment can be formed of any pliable material, e.g., an electroactive polymer, a shape memory material such as Nitinol, etc., and can be attached to a distal end of the rigid proximal portion of the actuator 82 in any way, e.g., crimped, tied, etc. The flexible segment can extend distally from the actuator 82 through the articulating distal portion of the shaft 20 to the end effector 22. The distal, flexible segment of the translator element can be coupled to the end effector 22 to allow actuation of the end effector 22, e.g., opening and closing the jaws 16a, 16b, in response to translation of the actuator 82. The flexible extension of the actuator 82 through the articulating region of the shaft 20 can provide for control of the end effector 22, yet allows for the articulation of the shaft 20 at the articulation joints 42, 44. By extending through the shaft 20 with the shaft 20 in either the straight or articulated configuration, the flexible extension can also allow the end effector 22 to be rotated about the shaft's longitudinal axis 20A relative to the shaft 20. When the shaft 20 is in the articulated configuration, the end effector's rotational axis includes the shaft's longitudinal axis 30A at the second linkage 30.

As will be appreciated by a person skilled in the art, the handle 12 can include any rotating mechanism configured to rotate the end effector 22, such as a knob 92 as shown, a lever, a wired or wireless electronic control, etc. The knob 92 can be configured to rotate the actuator 82 a full 360° clockwise and/or counterclockwise to correspondingly rotate the end effector 22 a full 360° clockwise and/or counterclockwise about the second linkage's longitudinal axis 30A, which as mentioned above is the same as the shaft's longitudinal axis 20A when the shaft 20 is in the straight configuration. A lock such as a button 90 can be included on the handle 12 for closing and holding the position of the thumb trigger 84 to maintain the end effector 22 in a particular state. The handle 12 can include a second rotating mechanism, e.g., a second knob 96 coupled to a proximal end of the shaft 20, for rotating the shaft 20 360° about the shaft's longitudinal axis 20A. A bushing 100 can surround the proximal rod 48 distal of the carriage 70 for rotating the proximal rod 48 and hence the shaft 20 relative to the carriage 70. The knobs 92, 96 can thus allow for separate, relative rotation between the shaft 20 and the end effector 22. The shaft 20 can be rotated in both the straight and articulated configurations to further increase the positioning range of the end effector 22. Such rotation of the shaft 20 and/or the end effector 22 can help optimally position the shaft's distal portion 20d within a body before and/or after the shaft 20 is articulated.

Figure 11:
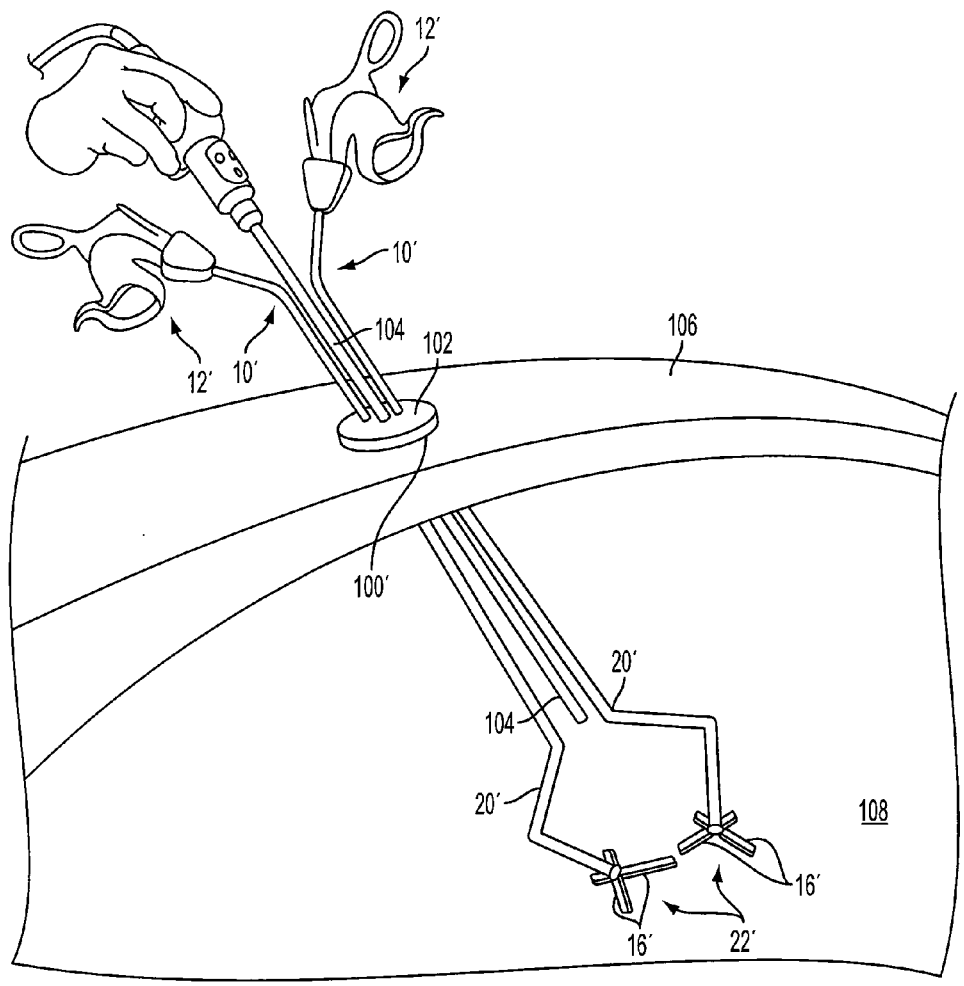
FIG. 11 is a perspective, partially cross-sectional view of a surgical access device positioned within a tissue opening and having two laparoscopic devices and a scoping device inserted therethrough and positioned within a body cavity, the laparoscopic devices each having a shaft in an articulated configuration.

In use, as shown in an exemplary embodiment in FIG. 11, one or more surgical devices 10' can be inserted through an opening 100' in tissue 106 to access a body cavity 108 underlying the tissue 106 where the devices 10' can perform any type of surgical procedure. The devices 10' can generally each be configured and used similar to the device 10 of FIGS. 1-10. However, in this illustrated embodiment, a proximal portion of each device's shaft 20' just distal of a handle 12' has a bend or curvature, which as mentioned above can help facilitate positioning of the devices 10' and prevent interference therebetween. Also as mentioned above, a person skilled in the art will appreciate that while the devices 10' are shown in the illustrated embodiment in use in a laparoscopic procedure and inserted into the body cavity 108, e.g., the abdominal cavity, through a multiple port access device 102 positioned in the tissue opening 100', e.g., an incision at the navel, any of the surgical devices disclosed herein can be used in a variety of surgical procedures and inserted into a patient's body in any number of ways. Prior to insertion of any instruments through the multiple port access device 102, insufflation can be provided through an insufflation port, as will be appreciated by a person skilled in the art. A scoping device 104 can also be inserted through the multiple port access device 102 to provide visualization. Non-limiting examples of a scoping device include an endoscope, a laparoscope, and a colonoscope.

The multiple port access device 102 can include multiple instrument openings each configured to receive an instrument inserted therethrough. Each opening can have an associated sealing port that can be configured to provide at least one instrument seal that forms a seal around an instrument disposed therethrough, but otherwise does not form a seal when no instrument is disposed therethrough, at least one channel seal or zero-closure seal that seals a working channel created by the sealing port when no instrument is disposed therethrough, or a combination instrument seal and channel seal that is effective to both form a seal around an instrument disposed therethrough and to form a seal in the working channel when no instrument is disposed therethrough. Exemplary embodiments of multiple port access devices are described in more detail in U.S. patent application Ser. No. 12/399,482 filed Mar. 6, 2009 entitled "Methods And Devices For Providing Access Into A Body Cavity," U.S. patent application Ser. No. 12/399,473 filed Mar. 6, 2009 entitled "Methods And Devices For Providing Access Into A Body Cavity," U.S. patent application Ser. No. 12/512,542 filed Jul. 30, 2009 entitled "Methods And Devices For Providing Access Into A Body Cavity," U.S. patent application Ser. No. 12/512,568 filed Jul. 30, 2009 entitled "Methods And Devices For Providing Access Into A Body Cavity," U.S. patent application Ser. No. 12/399,633 filed Mar. 6, 2009 entitled "Methods And Devices For Providing Access Into A Body Cavity," U.S. patent application Ser. No. 12/399,625 filed Mar. 6, 2009 entitled "Methods And Devices For Providing Access Into A Body Cavity," U.S. patent application Ser. No. 12/399,547 filed Mar. 6, 2009 entitled "Surgical Access Devices And Methods Providing Seal Movement In Predefined Paths," U.S. patent application Ser. No. 12/399,656 filed Mar. 6, 2009 entitled "Surgical Access Devices And Methods Providing Seal Movement In Predefined Movement Regions," and U.S. patent application Ser. No. 12/766,086 filed Apr. 23, 2010 entitled "Methods And Devices For Accessing A Body Cavity," which are hereby incorporated by reference in their entireties.

Figure 12:
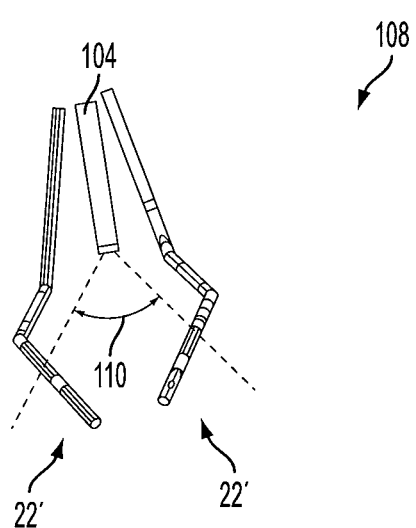
FIG. 12 is a side view of distal portions of the laparoscopic devices and the scoping device of FIG. 11 positioned in the body cavity.

The devices 10' can be simultaneously or sequentially inserted through the multiple port access device 102 with the shafts 20' in straight configurations to position distal portions of the shafts 20' within the body cavity 108. The shafts 20' inserted through the multiple port access device 102 can each extend generally parallel to one another, e.g., have parallel longitudinal axes. After distal portions of the shafts 20' have been positioned within the body cavity 108, the handles 12' of the devices 10' can be manipulated, simultaneously or sequentially, to move the shafts 20' from straight configurations to articulated configurations and to allow the end effectors 22' at respective distal ends of the shafts 20' to be brought together in a non-interfering, cooperative, facing relationship and to be within a viewing range 110 of the scoping device 104, as also illustrated in FIG. 12. The shafts 20' can be articulated any amount, including not at all, same or different from one another, and can be selectively adjusted during the surgical procedure to form larger or smaller compound angles as desired. The shafts 20' can also be rotated relative to the handles 12', the end effectors 22' can be rotated relative to the shafts 20', and the end effectors' jaws 16' can be opened and closed. The devices 10' can thus allow the shafts 20' to be easily inserted into a body in straight configurations through a single, relatively small opening 100' with the shafts 20' being substantially parallel, and the shafts 20' can be subsequently articulated to optimally position the end effectors 22' relative to the surgical site, to each other, to the scoping device 104, and to any other tools within the body cavity 108. Because the device 10' can be articulated, its end effector 22' can be positioned at an angle with respect to a remainder of the shaft 20' thereof, triangulation and visualization can be improved. In other words, even though the devices 10' and the scoping device 104 are inserted through a common incision, it is still possible to see the end effectors 22' of the devices 10' and to bring the end effectors 22' of the two instruments devices 10' together in a facing relationship at a single point within the body cavity 108.

In addition, because the handles 12' can be bent with respect to the shafts 20', maneuverability can be improved, e.g., the "chopstick" effect can be reduced, since interference between the handles 12' of the two devices 10' can be avoided. Finally, user comfort can be enhanced, since the bend angles of the devices 10' adjacent the handles 12' can be customized at any time before or during the surgery.

The shafts 20' can also be easily removed from the patient's body by moving the shafts 20' from articulated configurations to straight configurations. The multiple port access device 102 can be configured to allow further adjustment of instruments inserted therethrough, such as by allowing collective rotation of the instruments around a central axis of the multiple port access device 102.

A proximal housing portion of the multiple port access device 102 can be configured to be removable from a distal retractor portion of the multiple port access device 102. Thus, at any point before, during, or after a surgical procedure, the proximal housing portion can in full or part be released from the distal retractor portion, and the distal retractor portion can be removed from the tissue 106. With the proximal housing portion of the multiple port access device 102 disengaged from the distal retractor portion and with the distal retractor portion still positioned in the tissue opening 100', a working channel of the distal retractor portion can provide access to the body cavity 108 underlying the tissue 106. One or more of the devices 10' and/or other surgical instruments can be advanced through the working channel, such as a waste removal bag configured to hold waste material, e.g., dissected tissue, excess fluid, etc., from the body cavity 108. The bag can be introduced into the body cavity 108 through the distal retractor portion's working channel or other access port. A person skilled in the art will appreciate that one or more surgical instruments can be advanced through the distal retractor portion's working channel before and/or after the proximal housing portion has been attached to the distal retractor portion. A surgical drape can optionally be placed over the distal retractor portion and the tissue opening 100' during removal of the distal retractor portion to help reduce dispersion of bodily fluid outside the surgical space.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a handle, a proximal housing portion of a surgical access device, an end effector, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An articulating laparoscopic device, comprising:
   an elongate shaft having first and second articulation joints, the first articulation joint being configured to pivot in a first direction and the second articulation joint being configured to pivot in a second direction that is opposite to the first direction such that the shaft is configured to form a compound angle, one of the first and second directions being clockwise and another of the first and second directions being counterclockwise, the first articulation joint being limited to pivoting from a zero angle position in the first direction to form the compound angle, and the second articulation joint being limited to pivoting from a zero angle position in the second direction to form the compound angle;
   an end effector coupled to a distal end of the elongate shaft and positioned distal of the first and second articulation joints, the end effector being pivotable relative to the elongate shaft at a third articulation joint positioned distal of the first and second articulation joints;
   an articulator element extending through the elongate shaft and configured to rigidly maintain the elongate shaft in a plurality of positions in which the elongate shaft has the compound angle;
   wherein movement of the articulator element relative to the elongate shaft is configured to simultaneously pivot the first articulation joint in the first direction and the second articulation joint in the second direction to form the compound angle.

2. The device of claim 1, wherein the articulator element is rigid.

3. The device of claim 1, wherein the second articulation joint is movable toward and away from a longitudinal axis of the elongate shaft, and the first articulation joint is limited to longitudinal movement along an axis substantially parallel to the longitudinal axis of the elongate shaft.

4. The device of claim 1, wherein the elongate shaft includes:
   a main shaft extending from a handle;
   a first linkage having a proximal end coupled to a distal end of the main shaft at the first articulation joint; and
   a second linkage having a proximal end coupled to a distal end of the first linkage at the second articulation joint.

5. The device of claim 4, wherein the first and second linkages are movable between an initial position in which the first and second linkages are longitudinally aligned with a longitudinal axis of the elongate shaft and an articulated position in which the first and second linkages are angularly oriented relative to the longitudinal axis of the elongate shaft.

6. The device of claim 1, wherein the articulator element comprises first and second articulation rods extending through the elongate shaft and being pivotally coupled to one another at a pivot point.

7. The device of claim 6, wherein the pivot point floats laterally relative to the elongate shaft.

8. The device of claim 6, wherein the articulator element includes a pin that extends into a cam slot formed in a portion of the elongate shaft for guiding movement of the articulator element relative to the elongate shaft.

9. The device of claim 1, wherein the end effector comprises graspers having opposed jaws, and the elongate shaft includes a flexible actuator element extending therethrough and being effective to move the opposed jaws between a closed position and an open position.

10. The device of claim 1, wherein the first articulation joint includes a first pivot point and the second articulation joint includes a second pivot point, the first and second pivot points being positioned offset from a central longitudinal axis of the elongate shaft when the elongate shaft is in a substantially straightened position.

11. An articulating laparoscopic device, comprising:
    an elongate shaft;
    a first linkage coupled to a distal end of the elongate shaft at a first articulation joint, the first linkage including a slot formed therein;
    a second linkage coupled to a distal end of the first linkage at a second articulation joint; and
    an articulator element having a proximal articulation rod extending through the elongate shaft and having a pin slidably extending into the slot formed in the first linkage such that sliding movement of the in causes articulation of the first linkage, and the articulator element having a distal articulation rod extending through the first linkage and having a proximal end pivotally coupled to a distal end of the proximal articulation rod at a single pivot point that floats laterally relative to the elongate shaft and the first linkage, and a distal end of the distal articulation rod being coupled to the second linkage.

12. The device of claim 11, wherein the proximal articulation rod is configured to translate longitudinally relative to the elongate shaft and the distal articulation rod is configured to translate laterally relative to the first linkage.

13. The device of claim 11, wherein the slot formed in the first linkage comprises a curved cam slot.

14. The device of claim 11, further comprising an end effector coupled to a distal end of the second linkage.

15. The device of claim 14, wherein the end effector includes opposed jaws, and the device includes an actuator element extending through the elongate shaft, the first linkage, and the second linkage and coupled to a proximal end of the opposed jaws, the actuator element being configured to move the opposed jaws between a closed position and an open position.

16. The device of claim 11, wherein the pivot point is configured to float laterally relative to the elongate shaft and the first linkage by moving toward and away from a longitudinal axis of the elongate shaft and moving toward and away from a longitudinal axis of the first linkage.

17. The device of claim 11, wherein the pivot point is detached from the first linkage.

18. The device of claim 11, further comprising a gap between at least one of a first and a second arms providing space for the single pivot point to move laterally.

19. An articulating laparoscopic device, comprising:
an elongate shaft;
a first linkage having a proximal end coupled to a distal end of the elongate shaft at a first articulation joint, the first articulation joint being laterally offset from a longitudinal axis of the elongate shaft;
a second linkage having a proximal end coupled to a distal end of the first linkage at a second articulation joint, the second articulation joint being laterally offset from the longitudinal axis of the elongate shaft, and the second articulation joint being movable toward and away from the longitudinal axis of the elongate shaft such that the first and second linkages are movable between an initial position in which the first and second linkages are longitudinally aligned with the longitudinal axis of the elongate shaft and an articulated position in which the first and second linkages are angularly oriented relative to the longitudinal axis of the elongate shaft;
an end effector coupled to a distal end of the second linkage; and
a rigid articulator element having a proximal portion disposed within the elongate shaft and configured to translate longitudinally relative to the elongate shaft, and a distal portion disposed within the first linkage and configured to translate laterally relative to the first linkage.

20. The device of claim 19, wherein the articulator element is configured to rigidly maintain the first and second linkages in a fixed angular orientation through an entire range of motion of the first and second linkages between the initial and articulated positions.

21. The device of claim 19, wherein the proximal portion of the articulator element is coupled to the distal portion of the articulator element at a pivot point that is movable laterally relative to the elongate shaft and the first linkage.

22. The device of 19, wherein movement of the rigid articulator element relative to the elongate shaft is configured to pivot the first linkage in a first direction and pivot the second linkage in a second, opposite direction.

* * * * *